(12) United States Patent
Yoo

(10) Patent No.: US 10,307,758 B2
(45) Date of Patent: Jun. 4, 2019

(54) THIN FILM VALVE APPARATUS USING A FLUID HOLE CLOSING MEMBRANE

(71) Applicants: RESEARCH BUSINESS FOUNDATION SUNGKYUNKWAN UNIVERSITY, Gyeonggi-do (KR); CDGENE Inc., Suwon-si (KR)

(72) Inventor: Jae Chern Yoo, Gwacheon-si (KR)

(73) Assignees: Research & Business Foundation Sungkyunkwan University, Suwon-si (KR); CDgene Inc., Suwon-si (KR)

( * ) Notice: Subject to any disclaimer, the term of this patent is extended or adjusted under 35 U.S.C. 154(b) by 571 days.

(21) Appl. No.: 14/732,664

(22) Filed: Jun. 5, 2015

(65) Prior Publication Data
US 2015/0375226 A1    Dec. 31, 2015

Related U.S. Application Data

(63) Continuation of application No. PCT/KR2013/011159, filed on Dec. 4, 2013.

(30) Foreign Application Priority Data

Dec. 5, 2012  (KR) .................. 10-2012-0140529

(51) Int. Cl.
*B01L 3/00* (2006.01)
*G01J 1/02* (2006.01)
(Continued)

(52) U.S. Cl.
CPC ...... *B01L 3/502738* (2013.01); *F16K 99/003* (2013.01); *F16K 99/004* (2013.01);
(Continued)

(58) Field of Classification Search
CPC .... F16K 99/001; F16K 99/003; F16K 99/004; F16K 2099/008; F16K 2099/0082;
(Continued)

(56) References Cited

U.S. PATENT DOCUMENTS 3,335,946 A    8/1967  Putterlik et al.
3,628,767 A   12/1971  Lombard et al.
(Continued)

FOREIGN PATENT DOCUMENTS

CN   101873885 A   10/2010
GB     1075800 B1    7/1967
(Continued)

OTHER PUBLICATIONS

Park, Jong-Myeon, et al. "Multifunctional microvalves control by optical illumination on nanoheaters and its application in centrifugal microfluidic devices." Lab on a Chip 7.5 (2007): 557-564.*
(Continued)

*Primary Examiner* — Robert J Eom
(74) *Attorney, Agent, or Firm* — NSIP Law

(57) ABSTRACT

A thin film valve includes at least one chamber for storing a fluid required for biological/chemical analysis, a plurality of chamber for performing a biological/biochemical reaction, or connecting, at least one chamber performing the biological or biochemical reaction to enable a movement of the fluid flow, a flow path arranged to communicate with the hole on the flow path, a thin film closing membrane for closing the fluid hole, a thin film valve including the hole and the fluid hole closing membrane, a multilayered plurality of substrates forming the fluid path, the fluid hole and the chamber, a rotatable disk forming the fluid path, fluid hole, the plurality of chambers, a heat generator, laser beam generator heating the thin film valves, a light detector for detecting amount of light passing through the membrane and closing the fluid hole, and a feedback controller for controlling the focusing actuator.

12 Claims, 13 Drawing Sheets

(51) Int. Cl.
*F16K 99/00* (2006.01)
*G01N 35/00* (2006.01)
*G01N 35/10* (2006.01)

(52) U.S. Cl.
CPC ...... *G01J 1/0204* (2013.01); *G01N 35/00069* (2013.01); *G01N 35/1002* (2013.01); *G01N 35/1097* (2013.01); *B01L 2200/143* (2013.01); *B01L 2300/0803* (2013.01); *B01L 2300/087* (2013.01); *B01L 2300/0874* (2013.01); *B01L 2300/0887* (2013.01); *B01L 2300/12* (2013.01); *B01L 2300/1827* (2013.01); *B01L 2300/1861* (2013.01); *B01L 2400/0409* (2013.01); *B01L 2400/0683* (2013.01); *F16K 2099/008* (2013.01); *F16K 2099/0084* (2013.01); *G01N 2035/00247* (2013.01); *G01N 2035/00267* (2013.01)

(58) Field of Classification Search
CPC ........... F16K 2099/0084; G01J 1/0204; G01N 35/00069; G01N 35/1002; G01N 35/1097; G01N 2035/00247; G01N 2035/00267; B01L 3/502738; B01L 2200/143; B01L 2300/0803; B01L 2300/0807; B01L 2300/0874; B01L 2300/0887; B01L 2300/12; B01L 2300/1827; B01L 2300/1861; B01L 2400/0409; B01L 2400/0683
See application file for complete search history.

(56) References Cited

U.S. PATENT DOCUMENTS

| | | |
|---|---|---|
| 6,812,457 B2 | 11/2004 | Andersson et al. |
| 7,998,433 B2 | 8/2011 | Park et al. |
| 2008/0152546 A1* | 6/2008 | Bedingham ....... B01L 3/502738 422/400 |
| 2009/0317896 A1* | 12/2009 | Yoo .................. B01L 3/502738 435/287.1 |

FOREIGN PATENT DOCUMENTS

| | | |
|---|---|---|
| KR | 1020080097763 A | 6/2008 |
| KR | 1020100043956 A | 4/2010 |
| KR | 1020110073381 A | 6/2011 |
| WO | 2009/066897 A2 | 5/2009 |

OTHER PUBLICATIONS

Office Action dated Jun. 28, 2016 of Chinese Patent Application No. CN 101873885 A, which corresponds a the above referenced application.

Office Action dated Jun. 28, 2016 of China Patent Application No. CN 101873885 A, which corresponds to the above referenced application.

Chinese Office Action dated Jun. 28, 2016 in counterpart Chinese Patent Application No. 201380068405.2 (7 pages in English, 4 pages in Chinese).

* cited by examiner

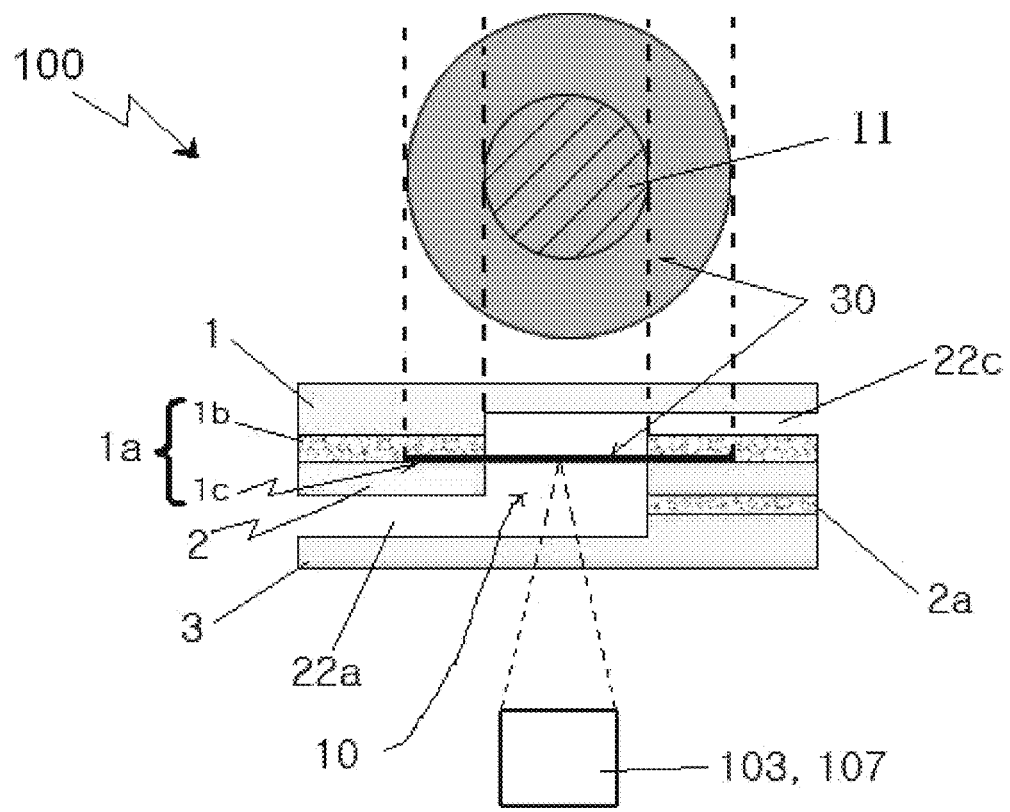

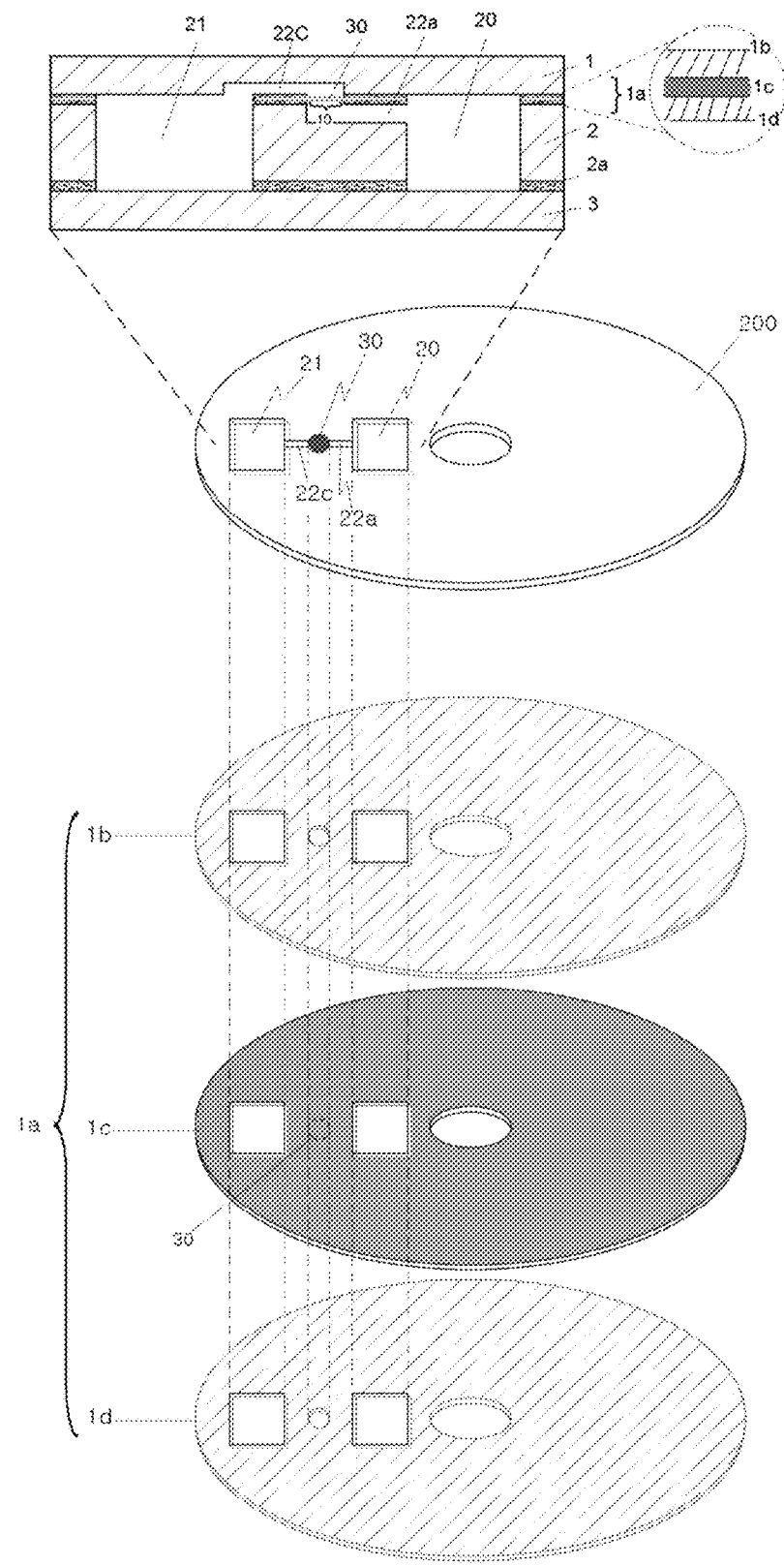

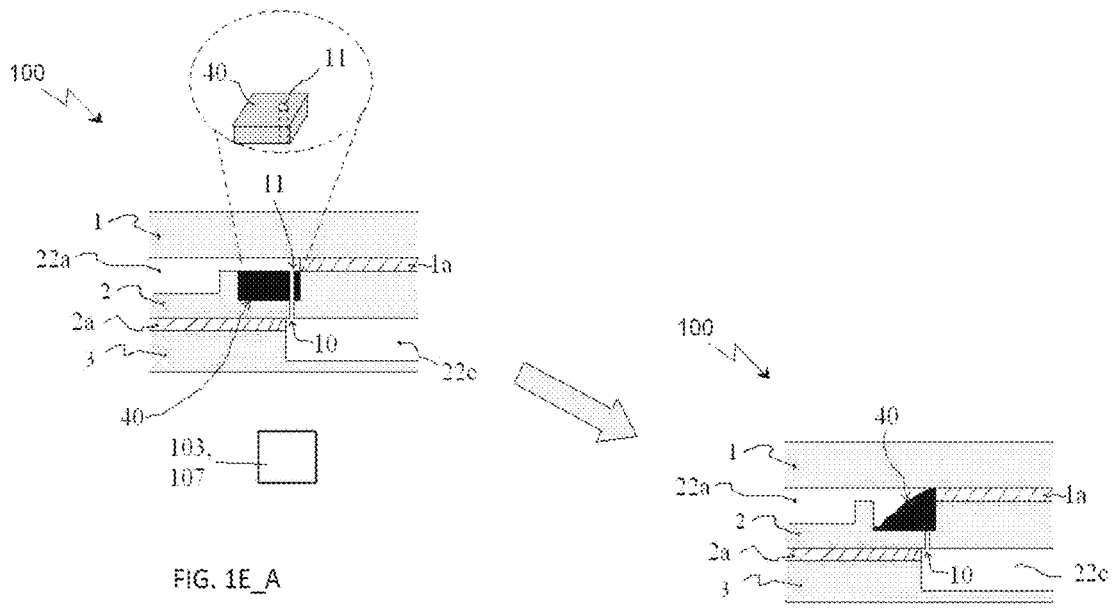
FIG. 1E_A
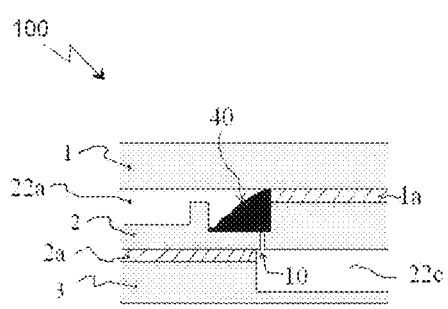
centrifugal force
FIG. 1E_B
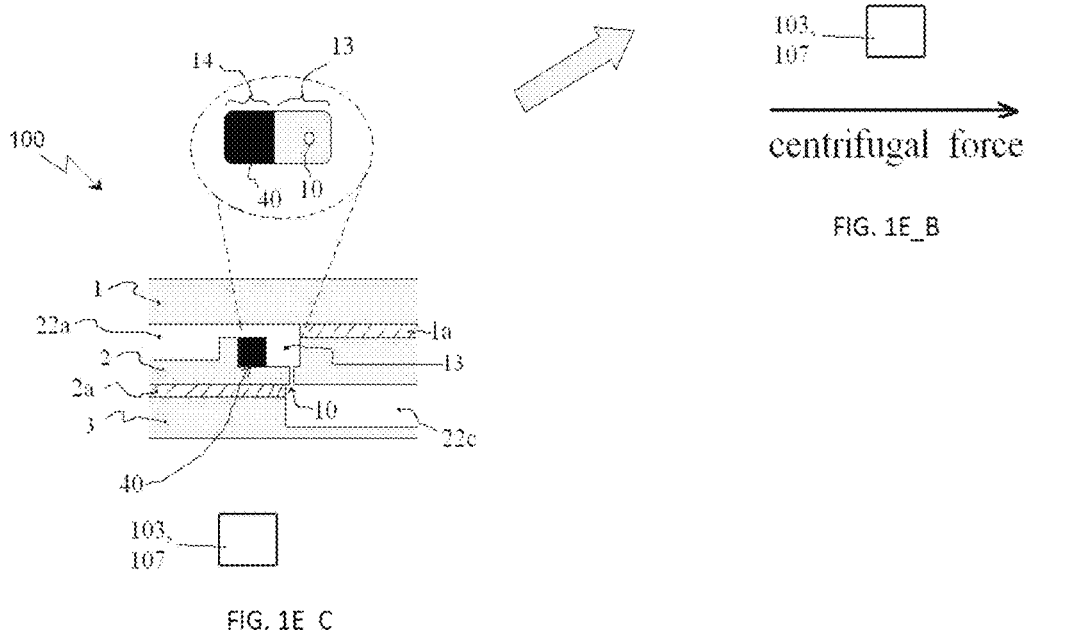
FIG. 1E_C

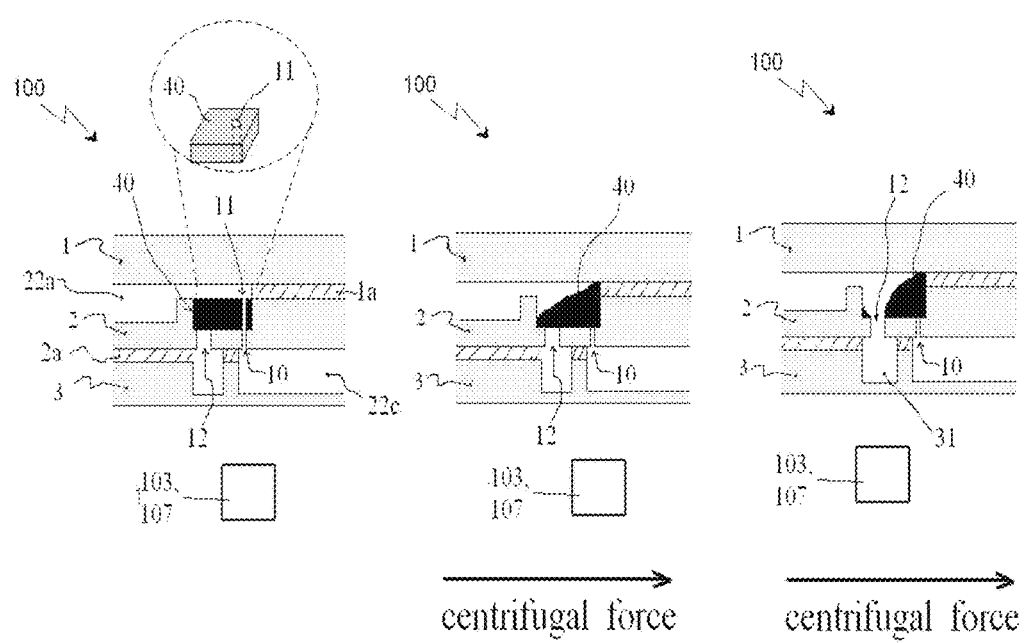
FIG. 1F_A  FIG. 1F_B  FIG. 1F_C

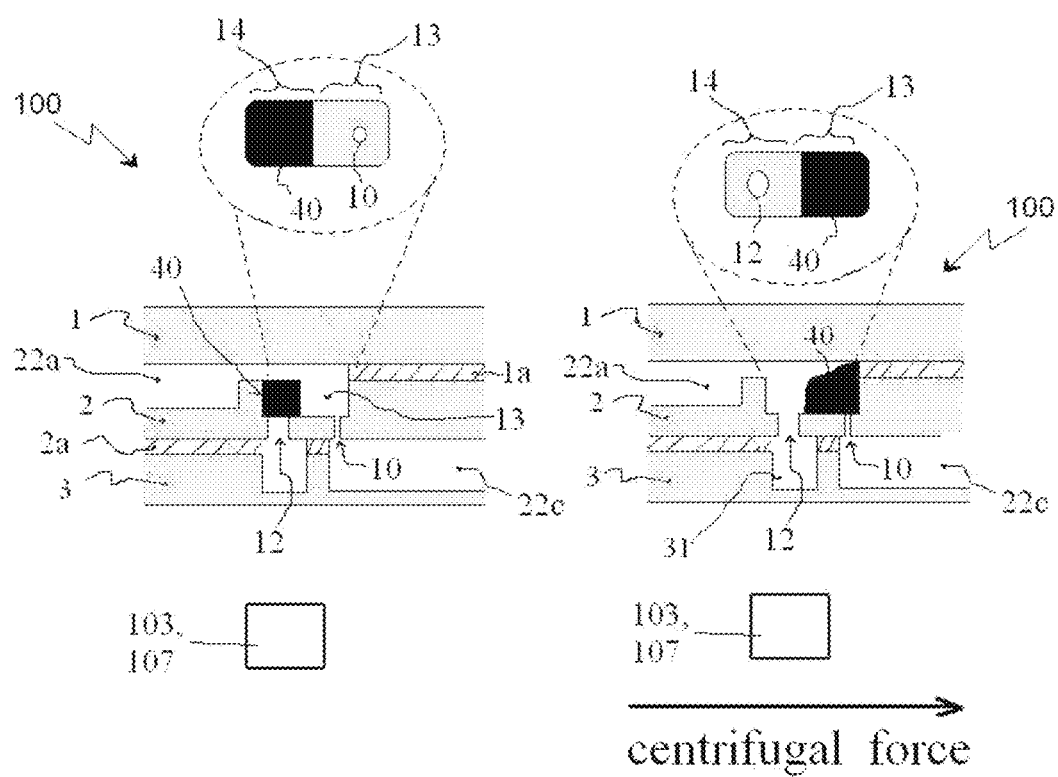
FIG. 1G_A      FIG. 1G_B

THIN FILM VALVE APPARATUS USING A FLUID HOLE CLOSING MEMBRANE

CROSS-REFERENCE TO RELATED APPLICATIONS

This is a continuation of PCT International Application No.: PCT/KR/2013/011159, filed on Dec. 4, 2013, which claims foreign priority to Korean Patent Application No.: 10-2012-0140529, filed on Dec. 5, 2012, in the Korean Intellectual Property Office, both of which are hereby incorporated by reference in their entireties.

TECHNICAL FIELD

Embodiments of the invention relate to the thin film valve apparatus and the method thereof relating to the on/off control system of a fluid hole using a thin film closing membrane for controlling the flow or the flow rate of a fluid, more particularly the fluid hole and the fluid path are opened or closed by melting the thin film closing membrane with a heat from heating generator.

BACKGROUND OF ART

In the most of clinical diagnosis analysis equipment for inside of fluid a small amount of analyzer detection till the recent, by designing the apparatus for designing the multiple sample preparation and automated apparatus for the reagent addition and analyzing the parallel or the numerous test sample the effectiveness and economical efficiency were improved. The automated reagent preparation apparatus and such automated analyzer are integrated in the single thin film apparatus. The thin film type clinical test analyzer of this form automatically accurately can perform the hundreds kinds analysis with automatic or half having a small amount of sample and reagent within the one-hour. But this thin film type analyzer has the problem that the design is difficult to the design be complicated and the valve for automatically supplying sample or reagent the enzyme and buffer solution to the desired position on the thin film type analyzer essentials thin than. Therefore, it is simple in order to overcome this problem. It desperately need the suitable membrane valve for the thin film type analyzer.

In general, looking at the CD and DVD used as the film substrate, 12 cm polycarbonate substrate, the standard compact disk is formed from a reflective metal layer and a protective lacquer coating. DVD, CD and CDROM format is described by ISO 9660 industrial standard.

The polycarbonate substrate is optical quality transparent polycarbonate. Data layer of the DVD and CD are part of the polycarbonate substrate and the data is decorated with a series of pits shape by a stamper during the injection molding process. The polycarbonate substrate is available, such as bio-fluid in the small amount of material in the form of a thin film analyzer to diagnose and detect strain modifications, when the place of pits on the disk during the injection molding process, the flow path in the fluid flow and a buffer solution of the chamber to store the chamber can be formed. Finally, bio disc is manufactured by bonding multi-layered discs.

A bio disk is needed to facilitate a thin film valve controlling the flow and flow rate of the fluid flow path formed in the bio disk.

Hereinafter, the conventional CD-ROM, a disk, such as DVD to convert modified lab-on-a-chip to diagnose and detect a small amount of substance in the fluid Lab On a Chip, a protein chip and DNA chip, a biochip such as the valve is integrated with a thin film disk or a disk with a thin film integrated valve for performing bio and chemical processes to diagnose and detect a small amount of material in the fluid; And it refers to a device with a control unit for controlling the drive referred to as "thin film valve device".

By using the centrifugal force of the injected sample to the inlet on the disk, a device for moving the fluid to the surface of the disk, the European patent "Disk for centrifuge" GB1075800, publication date 1967 Jul. 12 are disclosed. In addition, the fluid going by using the centrifugal force the sample injected into the inlet of the disk to move to the channel and the chamber, a device for separating the sample European patent "Separating Disks for centrifuge" EP Patent No. 3,335,946, Apr. 12, 1965 are disclosed. However, these inventions have failed to elaborate flow control since the invention could not overcome the delamination problem of the valve.

In addition, an electromagnetic valve is used to open and close the flow path using a cylinder or moving the plunger by a force of a magnetic field. For moving the print cylinder or plunger, a suitable size of ferrite core and the number of winding are required to ensure the strength of the magnetic and also more power is needed for moving the cylinder or plunger to on-off valve. Therefore, the valve with the electromagnet will not only be possible to configure the thin-film due to the size of the electromagnetic valve itself, there are many problems in a number of power consumption due to heat, it is not suitable as a film-like valve.

The electromagnetic valve with the U.S. "Electromagnet Ball valves U.S. Pat. No. 3,628,767 and the paper "an optimized electromagnetically activated micro ball valve", proceedings Sensor. Vol. 2, 405-408, 1999 has been a good example for using an electromagnetic valve.

Additionally, when the liquid meets a thin fluid path changing into a wide fluid path or when the surface changing from hydrophilic to hydrophobic, the capillary burst valve, exemplified in United States patent "Integrated microfluidic disk" U.S. Pat. No. 6,812,457, prevents liquid from completely spilling, even if the centrifugal force is generated, until the rotation speed of the disk exceeds a certain threshold.

The capillary burst valve can independently control each valve based on rotation speed and the width of the fluid path, shape, surface condition and the combination thereof. However, the capillary burst valve cannot be used in applications that have high speed rotation speed process because the opening critical rotation speed of the valve is very low and without meticulous speed control the valve may unintentionally be opened and when the number of independently controlled valves increase more meticulous rotation speed control is needed because the rotation speed difference between individual valves are very miniscule.

Additionally, even if meticulous speed control is possible, reproducibility of the valve control may not be possible because the rotation speed of each disk may be different due to variables in the disk creating process. Also, capillary burst valves have disadvantage of long term storage due to evaporation problems because they are not fundamentally sealed.

In order to solve the problems, the present invention provides thin film valve apparatus that combines multi-layered disk with thin film adhesive tape while creating perforated closing membrane on the perforated hole with black membrane layer then melting the thin film closing membrane with laser beam and opening the thin film closing membrane.

Solving Means of Problem

To achieve the same purpose of thin film valve apparatus of the present invention, the thin film adhesive tape of fluid hole closing membrane is metal coated thin film adhesive tape or black paint that include plurality of micro heating particle that absorb energy of the laser beam.

The black paint is easily heated by a laser beam because it has a high absorption rate coefficient.

A plurality of micro heating particles hated with radiation of laser beam fuse the adhesive.

The micro heating particles are preferred to have at least one type of particles selected from ferromagnetic material, the magnetic fluid, or a metal oxide.

The magnetic substance is preferred that the steel consisting of at least one selected from the group consisting of Fe, Ni, Cr and oxides thereof as a component.

Metal oxide is preferred to be selected from the group consisting of Al2O3, TiO2, Ta2O3, Fe2O3, Fe3O4 and HfO2.

The ferromagnetic powder called the magnetic fluid is the ultrafine particle 1 nm~100 nm is utilized. The liquid of the colloid state is preferred so that the liquid itself have magnetism using the surfactant like the fatty acid.

Adhesive used in the thin film adhesive tape is one sided tape, and the double sided tape or the adhesive tape are preferred. And the material like the hot melt, silicone, rubber, modified silicon, acryl group, polyamide, polyolefin, teflon-like, polyester, epoxy, the ultravilotic sense curing resin UV curable adhesive, UV adhesive, thermoplastic resin, gel, the wax etc. as to the adhesive, can be applied.

Generally, it surface-treated in both sides or one side of membrane such as one sided tape or the double sided tape is paper, vinyl, the polyester film, polyethylene film Polyethylene film PET the polyethylene terephthalate, and the Poly-Ethylene Terephthalate film and the other composite by the special adhesive an adhesive: a gluing agent. The high sealing and adhesive material having the characteristic of the shock-absorbing, vibrational relaxation, the impact resistance, heat resistance, adsorption capability, the adhesive force etc are selected according to the condition needed and it can use.

According to another aspect of the present invention, black membrane is used in the thin film adhesive tape of the fluid closing hole.

A black membrane increases the absorption rate and is easily heated by a laser beam.

According to an embodiment present invention, the hot melt tape or thermosetting tape or the thermoplastic tape is preferred.

The polyacrylamide, polyacrylate, polymethacrylate, and polyvinyl amides are preferred as a gel.

COC, PMMA, PC, PS, POM, PFA, PVC, PP, PET, PEEK, PA, PSU, and PVDF are preferred as a thermoplastic resin.

A paraffin wax, synthetic wax, and microcrystalline wax are preferred as a wax.

Another embodiment of the present invention provides a thin film valve apparatus comprising of fluid closing hole integrated with body of the rotatable disk, one or more chambers for storing biological or biochemical analysis, flow paths connecting the chambers, assay site or biochemical reaction chamber for performing sample and biological or biochemical reaction, fluid holes located in the middle connect by the fluid path, thin film valve for closing the fluid hole with fluid closing hole as well as thin film valves.

An embodiment of the present invention, biological or biochemical reaction refers to 3D structural change based on specific binding reaction between two bio-materials or ligand-receptor reaction or antigen-antibody reaction or immune response reaction or DNA hybridization reaction or biochemical reaction.

The biochemical reaction is for heating up DNA and performing the nucleic acid PCR. More specifically, the reaction includes blood, the virus, bio-material, and bacteria in which the specimen includes such as DNA or RNA.

The thin film valve apparatus according to the present invention is suitable for detecting or analyzing small amount of biochemical or chemical substance within fluid like lab on a chip implementing ELISA/CLISA analysis method, lab on a chip implementing rapid test method, or food poison bacteria inspection, residual antibiosis inspection, residual agricultural pesticide inspection, heavy metal in water inspection, GMO food inspection, food allergy inspection, pollutant inspection, colon *bacillus* or *salmonella* like bacteria inspection, paternity test, types of meat or place or origin inspection, small amount of biochemical or chemical substance inspection.

According to an embodiment of the present invention, the inspection of *bacillus* the colon *bacillus*, O157 bacteria, *pseudomonas aeruginosa, staphylococcus aureus, vibrio*, salmonellae inspection is preferred.

In the present invention, it is preferred to inspect most frequently used organic phosphorus or carbonate based insecticides among insecticides used among vegetables, fruits, greens.

According to an embodiment of the present invention, it is preferred that the bio-material is at least one of the materials selected from in the DNA, oligonucleotide, RNA, PNA, ligand, receptor, antigen, antibody, milk, urine, saliva, hair, crops and vegetable sample, and the meat sample, fishes sample, birds sample, the sewage the polluted water, domestic animals sample, foodstuff, food sample, mouth cell, tissue sample, saliva, semen, the protein, or the biomass.

The food ingredient refers to ingredients to make food, specifically ingredient for stew, noodles, making kimchi, making soup, ingredients including soup and etc.

It is preferred in the urine specimen that the thin film valve apparatus performs the leucocyte, blood, protein, nitrite, PH, specific gravity, glucose, ketone, ascorbic acid, urobilinogen, or bilirubin analysis.

Taking hair sample has an advantage over blood or urine analysis by accurately measuring historical record comprising of minerals, nutrients and accumulation of poisonous substances. Also, it is well known to those skilled in the art that it accurately analyzes long periods of deficit or excessive intake of inorganic substances and amount of poisonous substances.

According to an embodiment of the present invention, the disk of the thin film valve apparatus may be the diameter of 120 mm, 80 mm, 60 mm or 32 mm is preferred.

The thin film valve apparatus, according to an embodiment of the present invention, the substrate of 2 layer or 3 layer, which is laminated or welded, the disk of the thin film valve apparatus is formed with the multi-layer disk.

According to an embodiment of the present invention, thin film valve apparatus, it is preferred that an upper, intermediate and lower substrate combine forming layers creating fluid path, fluid hole or chamber form inside the disk's body. Specifically, upper fluid path between side chamber and fluid hole is engraved at a predetermine depth in the upper substrate, fluid hole is formed in the intermediate substrate, and lower fluid path between the other side chamber and fluid hole is engraved at a predetermined depth in the lower substrate.

According to an embodiment, the thin film valve apparatus of the present invention, as to the fluid path, the thin film fluid path by the thin film adhesive tape is preferred.

The advantage of forming the fluid path without the inlaid of body with the thin film adhesive tape is provided to the thin film.

the thin film valve apparatus of an embodiment of the present invention, preferably it is formed owing to the thin film adhesive tape in which the flow path shape is designed into the thin film between the layer of the substrates.

The thin film fluid path in the part in which it is tightly bonded with each other with the thin film adhesive tape and it is comprised one body and at this time, the thin film adhesive tape comes off in the thin film between the support layer are formed at substrates.

The depth of the fluid path very narrowly can establish in the thin film. Therefore the capillary phenomena well occurs and the depth is advantageous for the fluid translation.

It coats the hydrophobicity on the fluid path of the valve front end in order to avoid the difficulty of the opening of the valve liquid filled the fluid path before the fluid hole closing membrane opening with the capillary phenomena.

The disk as to the thin film valve apparatus of the present invention, is the pneumatic pressure due to the movement of fluid may be referred to the be desirable, more, the be desirable the exhaust pipe is arranged as the opposite direction in other words, the opposite direction of the centrifugal force of the fluid flux the exhaust pipe for ejecting further is included.

As to the thin film valve apparatus of the present invention, it comprises the material selected in group comprised of the disk is the silicone, and air the gel aerogel, plastic, PMMA, glass, silicone, polypropylene, polyacrylate, polyvinyl alcohol, polyethylene, the polymethyl methacrylate PMMA:polymethyl methacrylate, the COC cyclic olefin polymer: Cyclic Olefin Copolymer and polycarbonate.

According to an embodiment of the present invention, COC and polycarbonate are most preferred while the disk the silicone, polypropylene, COC and polycarbonate are preferred.

Moreover, it is preferred that the disk surface of the thin film valve apparatus is coated with aluminum sheet or oil film to prevent liquid stored within the chamber from evaporating.

According to an embodiment of the present invention, the thin film valve apparatus includes forming the fluid path and hole between neighbor chambers, preparing thin film for closing the fluid hole, and thereafter making a hole at the thin film valve, by a heat from a heat source apparatus, to open the fluid hole.

According to an embodiment of the present invention, the thin film valve apparatus includes the fluid hole closing membrane by the thin film adhesive tape is left on the cell the membrane valve when forming substrate junction.

It is preferred that the black paint is coated on the fluid hole closing membrane region by the thin film adhesive tape.

According to an embodiment of the present invention, a black thin film adhesive tape comprised of adhesive layer and black membrane layer is used to create closing membrane on the fluid hole on the entire substrate region of the adhesive surface.

The adhesive layer may further include the black paint or micro heating particle.

According to an embodiment of the present invention, the thin film adhesive tape, includes of black membrane layer, covering the entire surface of the substrate, and adhesive layer, not covering the fluid hole closing membrane. At this time, the fluid hole closing membrane has the advantage that there is no adhesive layer and it easily melts with the laser beam.

According to an embodiment of the present invention, during bonding of substrate, fluid hole closing membrane can be formed by installing at least one of black vinyl, black hot melt adhesive, black thermoplastic resin, black polyester film, black paint coated PVDF, black polyethylene film, black PET the polyethylene terephthalate, and the Poly-Ethylene-Terephthalate film or other synthetic black materials.

The Material that is a thin film circular shape, and a thickness of 0.001 mm~0.2 mm is preferred.

While the body is assembled, the fluid hole closing membrane bonds the substrates, around the fluid hole and closing the fluid hole and opening by the heat of the laser beam.

According to an embodiment of the present invention, the adhesive bonds a plurality of membrane coated substrates to form a single body.

According to an embodiment of the present invention, the controller unit of the thin film valve apparatus includes the spindle motor for rotating a body, a slider on which the laser beam generator mounted, and a slide motor for moving the laser beam generator to a corresponding the fluid hole region by controlling a movement of the slider and opening the corresponding fluid closing membrane by the laser beam.

According to embodiments of the present invention, preferred methods of opening thin film valve includes method of radiating a laser beam to open a hole on the thin film closing membrane; moving the laser beam generating device from the left and right, and tearing the fluid thin film closing membrane while radiating a laser beam; or tearing the fluid hole closing membrane by slightly rotating a disk to the left and right while radiating a laser beam.

According to an embodiment of the present invention, the thin film valve controller mounts the permanent magnetic on the slide to search in a radial direction of area to be opened.

According to an embodiment of the present invention, space addressing of thin membrane valve is made through radial direction search and azimuthal direction search, where radial direction search is done by slider motor control and azimuthal direction search is done by short rotation control or step motor control for rotating predetermined rotation while the slider is stopped. In case of spindle motor, during short rotation, membrane cylinder magnet of disk and permanent magnet of slider stops disk's rotation and performs azimuth search and in case of stepping motor azimuth search information obtained from the reflector of the disk and photo coupler is used as reference to control rotating angle of the stepping motor for azimuth search.

In the state where the disk is stopped after the radial search and azimuth search done, opening a fluid hole by melting a thin film closing membrane of the corresponding membrane valve by a heat of the laser beam.

Preferably, according to an embodiment of the present, a control unit of the thin film valve apparatus may further include a thin film cylinder magnet on a disk providing the radial direction reference about the membrane valve, and a permanent magnet on a slider acting an attractive force about the thin film cylinder magnet.

Preferably, according to an embodiment of the present invention, the thin film valve apparatus may further include a reference reflector a radial direction reference about the membrane valve and a photo coupler detecting a position of the reference reflector.

It is preferred that a stepping motor, according to an embodiment, is connected on a spindle motor shaft with a gear for a rotation of the azimuthal direction of a body and operated.

After performing a search, a laser beam generator of the thin film valve apparatus is mounted on the slider, which melts a fluid hole closing membrane while rotating disk with a pulse beam or a continuous beam with radial search and makes a fluid hole.

In this case, during rotation of the disk, whenever laser beam generator apparatus, installed on the slide, matches or aligns with the thin film valve, without searching azimuth, the laser beam heats the fluid closing hole, opens the fluid closing hole.

A space addressing about a plurality of thin film membrane valve includes determining a reference point of the space addressing on a disk, placing a thin film cylinder magnet on the disk after the space addressing, and independently placing a laser beam generator to a corresponding membrane valve after the space addressing and opening a corresponding thin film valve.

According to an embodiment of the present invention, a space addressing about a plurality of membrane includes, providing a reference point of the space addressing on the disk as a coordinate of a reference reflector, detecting azimuth angle information of the reference point corresponding to a membrane valve using the photo coupler, after detecting, independently opening each thin film valve by moving a laser beam generator on a slider in a radial direction of the disk or and opening each membrane valve independently by disposing each laser beam generation system to each membrane valve.

As described above, in a case, if spacing address has been performed, the laser beam generating system and the thin film valve are aligned or spatially arranged, facing each other.

A neodymium magnet as a thin film cylinder magnet is preferred. However, it is not limited thereto.

The neodymium magnet is preferred but the permanent magnet can be replaced by an electromagnet.

In a state where the electromagnet on, a space dressing of thin film valve is performed by between the electromagnet and the thin film permanent magnet on the slider while rotating the disk with low speed according to an embodiment of the present invention.

According to an embodiment of the present invention, preferably, it is necessary to have a process which focuses parallel in order to use the laser as the heating source for melting the fluid hole closing membrane. The laser focusing processing includes, in order to focus, the lens is mounted on the front end of the laser beam generator, making the wedge shaped laser beam and focusing on the surface of the fluid hole closing membrane by swinging the laser beam generator to the disk in a vertical direction.

With mounting the laser beam generator on the lower part of the disk called the opposite side and the optical sensor on the upper portion of the disk, a laser focusing process includes, moving up the laser beam generator slowly whiling radiating on the disk with checking amount of beam inputting to the optical sensor, determining in-focus of the laser beam or the valve is open if the intensity of light becomes suddenly stronger, and stopping the movement of the laser bean generator finishing the laser focusing.

According to an embodiment of the present invention, the laser beam generator may further include a focusing actuator for the laser focusing.

According to an embodiment of the present invention, the laser beam generator may further include the focusing actuator for varying focusing distance and the feedback controller for observing an intensity and amount of the light passing through the thin film closing membrane with the optical sensor described above and reflecting this to the focusing actuator.

According to an embodiment of the present invention, the laser beam generator may further include the focusing actuator s to the invention, and, the other side, with forming the lens on the lower part substrate of the disk corresponding to the position of the valve into the hemi spherical grain in order to focus in this case, it is not necessary to have the focusing motion by up and down movement of the laser beam generation system.

According to an embodiment of the present invention, it is preferred that one of the optical sensor is used among a photo diode, a photodiode array, a charge-coupled device (CCD), a Complementary metal-oxide-semiconductor (CMOS) image sensor, and a laser power meter.

Effects of Invention

As illustrated in the above, the fluid hole of the body inner portion to the fluid path can be opened and can be closed as the invention relating to the opening/closing device of the tape applying the adhesive tape to the double sided tape which coats with the film or the black paint so that the thin film valve apparatus according to the present invention control the flow or the flow rate of fluid, and both sides of the black double sided tape or the black film or the fluid hole closing membrane formed with the film coating PVDF with the black paint with the heat source apparatus.

More specifically, the thin film valve apparatus according to the present invention is essential to the rotatable the bio disk in which bio-chip such as the lab on a chip for diagnosing inside of fluid a small amount of material and detecting, and the protein chip and DNA chip are integrated.

Particularly, the disk unit including the conventional CD-ROM and DVD etc is remodeled with deformation and the thin film valve apparatus of the present invention opens and closes the fluid path and the fluid hole formed in the body of the thin film but it is essential.

The thin film valve apparatus of the present invention provides the advantage the local heating is possible and it can accumulate there are many unit area per valves because of melting the thin film closing membrane using the laser beam and opening and In addition that the membrane valve by the thin film adhesive tape is automatically formed in the fluid hole region without the separate process while combining the multi-layer disk multi-layered disk with the thin film adhesive tape.

Because the present thin film valve apparatus using laser bean to open the fluid hole closing membrane by melting, not only can it integrate unit area per valves by enabling regional heating it also provides the advantage of automatically forming thin film valve near fluid hole by thin film adhesive tape without any special process during bonding multi-layered disc by thin film adhesive tape.

Therefore, it is suitable for the valve formation of the thin film type apparatus for the thin film valve apparatus of the present invention diagnosing the inside of fluid a small amount of material such as the Lab On a Chip or the DNA chip and detecting. Particularly, it is suitable for the fluid path which is remodeled with deformation and in which the disk unit including the conventional CD-ROM and DVD etc. is formed in the body of the thin film and the valve apparatus configuration of opening and closes the fluid hole or controlling the flow rate.

BRIEF EXPLANATION OF DRAWING

FIG. 1A and FIG. 1B is thin film valve using thin film adhesive tape according to an embodiment.

FIG. 1D shows fluid hole closing membrane in the disk phase using the double-sided adhesive tape according to an embodiment.

FIG. 1E_A, FIG. 1E_B, FIG. 1E_C, FIG. 1F_A, FIG. 1F_B, FIG. 1F_C, FIG. 1G_A, and FIG. 1G_B show the thin film valve uses black membrane utilizing black thermoplastic resin to open fluid hole.

DESCRIPTION OF EMBODIMENTS

Hereinafter, embodiments of the present invention will be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. Since purpose, characteristic, and other advantages like above of the present invention particularly explain the embodiment doing with desirable of the present invention with reference to the attached view it will become clearer.

Hereinafter, fluid hole according to an embodiment of the present invention will be describe.

The thin film valve apparatus using the attached fluid hole closing membrane according to a preferred embodiment of the present invention decides to be hereinafter particularly explained.

Figure 1A:
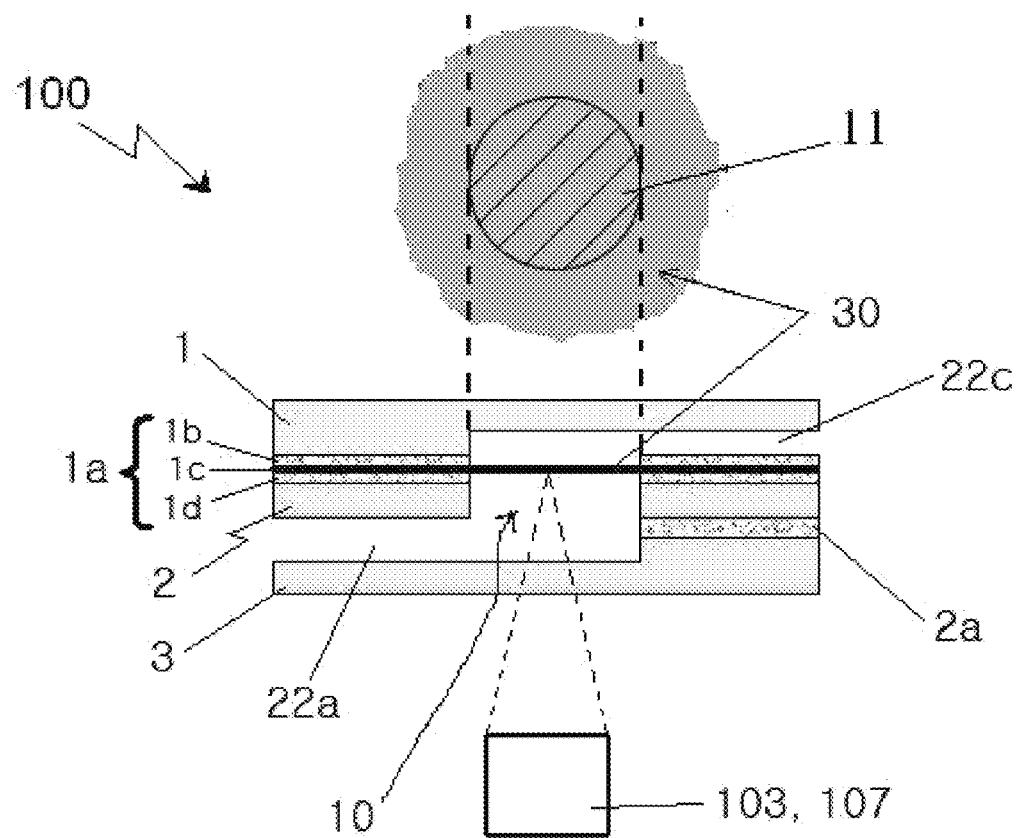

The configuration description of the thin film valve apparatus 100 using fluid hole closing membrane.
Description of Thin Film Valve 100 Using Fluid Hole Closing Membrane The above and other aspects will become more apparent by describing in detail exemplary embodiments thereof with reference to the attached drawings in which:

FIG. 1A and FIG. 1B show the cross-sectional view that another embodiment of the membrane valve using the thin film adhesive tape which includes the membrane valve 100 is implemented by the thin film closing membrane 30 in which three support layers 1, 2, 3 is formed by layered and bonding.

According to an embodiment of the present invention, thin film valve 100, for controlling fluid flow, accommodating a fluid hole closing membrane 30 on a region of a first fluid hole and opening a second fluid hole on the fluid closing membrane 30 by melting, tearing, or breaking a first fluid hole with laser beam's heat. The thin film valve 100 arranges a plurality of the first fluid holes 10 installed on the disk to be opened and closed independently. An embodiment of the present invention recommends 1 mm-5 mm diameter and 0.001 mm-0.2 mm width of fluid hole closing membrane 30, and a black body film or black membrane that easily melts or tears with low powered laser by absorbing all the light energy or generated from laser beam generator 107 or laser module 103.

Disk 200 of the FIG. 1D includes the upper portion substrate 1, and the intermediate substrate 2 and the lower part substrate 3. Fluid hole connecting the fluid paths channel, 22a, 22c in which each of them is the fluid in the substrate surface for the injection molding process flows, the chambers chamber, 20, and 21 which stores the buffer solution and the fluid path is formed with plural number. It is adhered so that substrates 1, 2, 3 stick to thin film adhesive tape layers 1a, 2a and forming a single body disk 200.

A DISK 200 of FIG. 1D having upper substrate 1, intermediate substrate 2 and lower substrate 3, during the injection molding process, forms a plurality of the first fluid hole that connect fluid holes or channels 22a, 22c for flowing fluid on the substrate surface, chambers 20, 21 for storing buffer fluid. The substrates 1, 2, 3 are bonded and multi-layered by a first adhesive tape 1a.

The Fluid hole closing membrane 30 of the thin film valve 100 is layered between the upper substrate 1 and intermediate substrate 2, formed on the a first fluid hole region 10 when bonded the substrates 1, 2 by the first thin film adhesive tape 1.

The intermediate 2 and the second thin film adhesive tape 2a which is layered between the lower part substrate 3 and combines substrates 2, 3 are included.

Specifically, chambers 20, 21 are formed on the lower substrate 3 and intermediate substrate 2, a first chamber 20 and a first fluid path engraved to the predetermined depth for connecting a first fluid hole are formed on the intermediate substrate 2, a second chamber 21 and a second fluid path 22c for connecting a first fluid hole 10 are formed on the upper substrate 1, a first fluid hole 10 is formed on the end parts of the fluid paths 22a, 22c for connecting the first chamber 20 and the second chamber 21.

The fluid hole 10 is closed by the fluid hole closing membrane 30. The fluid hole closing membrane 30 is formed on the fluid hole 10 when bonding the substrates 1, 2, and 3 with thin film adhesive tape 1a.

According to an embodiment of the present invention, the thin film valve apparatus includes a black body as the thin film closing membrane 30 is burnt with heat.

The thin film valve apparatus an embodiment of the present invention, the substrate junction is transparent blocks the laser and not heated when radiating light while thin film closing membrane 30 is black and easily destroyed by heat from source apparatus.

The light protection at the substrate junction is preferred by covered the upper portion substrate 1 of the disk substrate except for the perforation closing membrane or the lower part substrate 3 with CD label as a coating sheet or coated them with the light protector. Area except for the thin film closing membrane the laser beam is blocked by the CD label to the light barrier coating.

According to an embodiment of the present invention, the thin film valve apparatus includes completely blocking the first thin film hole 10 with the thin film closing membrane 30 for circulation and retention period, forming a second fluid path on the thin film closing membrane 30 and opened by the heat of the heater or heating apparatus, which is stored in the first chamber 20 with the rotation of the disk 200 and moved to the second chamber 21 with fluid pressure formed on the fluid itself.

The thin film closing membrane 30 has the advantage that the problem that the sealing is hindered does not occur among circulation and retention period with the reason like the evaporation of liquid because of well adapting to the expansion according to the environmental factors like the temperature and contraction since being pliable with the physical properties phase.

According to an embodiment of the present invention, it is preferred that in fluid paths 22a, 22c, the hydrophobic coating is preferred to prevent before opening the membrane valve from liquid being flowed into the first fluid hole 10 with the capillary phenomena.

The FIG. 1A-1B shows the first fluid hole 10 is closed (blocked) by the fluid hole closing membrane 30 and fluid paths 22a, 22c are blocked each other, if the first fluid hole 10 be opened and wants to connect fluid paths 22a, 22c, the fluid hole closing membrane 30 is melted and the first fluid hole 10 is opened by the second fluid hole is being formed by the laser beam generator 107 or the laser module 103.

According to an embodiment of the present invention, it is preferred that the first thin film adhesive tape 1a serves as the thin film closing membrane 30.

Referring to FIG. 1A, what foil-coats the first thin film adhesive tape 1a is preferred film coated on both sides of the black membrane 1c with adhesive layers 1b, 1d. Masked region of the fluid hole can be prevented from an adhesive coating when printing by a screen coating.

A thin film adhesive tape 1a includes composed of the black membrane 1c and an adhesive layer 1b, 1d which cover the entire surface of the substrate, the fluid hole closing membrane 30 only in part the adhesive layer is removed, and then the fluid hole closing membrane is formed by the black membrane 1c.

The fluid hole closing membrane 30 may include only black membrane layer 1c, the material of any one selected from the poly ethylene (PE), the polypropylene (PP), black hot melt adhesive, black thermoplastic resin, black vinyl, and the vinyl polyvinyl chloride (PVC).

FIG. 1B shows forming a fluid hole closing membrane 30 according to an embodiment of the present invention, a material of any one selected from a black plastic, black hot-melt adhesive, a black thermoplastic resin for installing a first fluid hole to form the fluid hole closing membrane 30.

Putting a material, any one selected from a black PE poly ethylene, a PP polypropylene, a black PVC vinyl polyvinyl chloride, and a black vinyl, into the first fluid hole region, when bonding a substrate, for forming the fluid hole closing membrane 30.

According to an embodiment of present invention, the black vinyl or the thin film adhesive tape further includes a micro heating particle.

According to an embodiment of the present invention, the fluid hole closing membrane 30 is formed by printing the first fluid hole 10 with the black paint to form a black film.

According to an embodiment of the present invention, the lower part of substrate 3 of the first fluid hole region 10 has a convex lens shape. The convex lens shape is a biconvex lens or a hemisphere convex lens can be used. The convex lens can be made to have convex lens on the lower part substrate 3 of the first fluid hole 10 in the injection molding process by designing.

According to an embodiment of the present invention, the first fluid region 10 of the substrate 1 may further include a reflective film reflector. it has the advantage in which the light passing through the first fluid hole more fuses the thin film closing membrane 30 by the quickly amount of the light coming in into the optical sensor and is checked the laser focusing goes well. The laser beam is in-focus and thin film closing membrane 30 is opened when the intensity of light becomes suddenly stronger over the reference limits, thereby, effectively controls the laser focusing. In the meantime, in this case, the optical sensor has to be installed in the laser beam generator and a reflection mode structure referring to FIG. 2F.

Figure 1C:
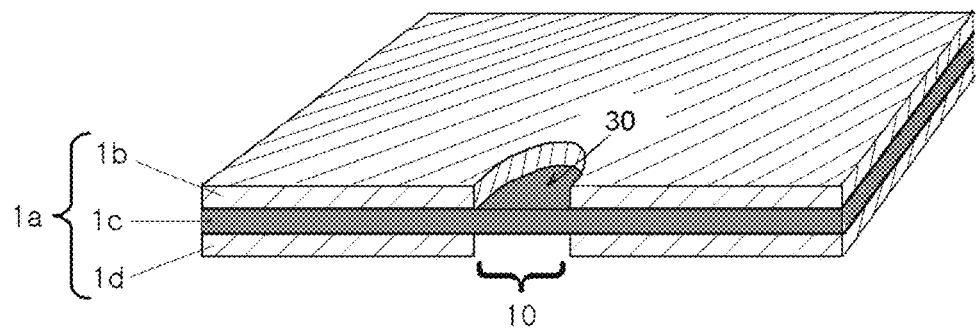
FIG. 1C shows two sided adhesive tape formed by using black membrane layer and adhesive membrane layer according to an embodiment.

FIG. 1C is a detail view of the black membrane layer 1c and the first thin film adhesive tape 1a formed using adhesive layers 1b, 1d.

Since the thin film closing membrane 30 is torn with the heating since only having the membrane layer 1c and since the membrane layer 1c is black or the micro heating particle is included and the other region, adhesive layers 1b, 1d in which are not heated by the laser beam from the laser beam generator 107 or the laser module 103, the adhesive layers neither physically changed nor torn.

FIG. 1D is an embodiment forming the thin film closing membrane 30 using the first thin film adhesive tape 1a on the disk 200.

It is preferred to be formed so that the first thin film adhesive tape 1a the membrane layer 1c be positioned between the upper portion adhesive layer 1b and lower part adhesive layer 1d. However, it is not limited thereto.

Firstly, if using the masking pattern having the opening part about area the fluid hole closing membrane 30 shape is removed, it prints on the membrane layer 1c with the adhesive with double side coating and the upper portion adhesive layer 1b and lower part adhesive layer 1d are formed for the thin film closing membrane 30 formation the rest membrane layer 1c area except for the first fluid hole region 10 is coated with the adhesive. Thereafter, the first thin film adhesive tape 1a of the part corresponding to chambers 20, 21 of the disk is removed with the laser cutting. The thin film closing membrane 30 is formed on the first fluid hole region 10 if the upper portion substrate 1 and intermediate 2 of the disk 200 are welded using this.

According to another embodiment of the present invention, a fluid hole closing membrane 30 formation method, includes printing one side of the membrane layer 1c with the adhesive and forming the upper portion adhesive layer 1b and membrane layer 1c the using the masking pattern having the opening part about area the thin film closing membrane 30 shape is taken out after doing the adhesion the rest membrane layer 1c area except for the first fluid hole region 10 is the lower part adhesive layer 1d in which the part which firstly comes under disk chambers 20, 21 for the fluid hole closing membrane 30 formation is removed coated in the upper side of the intermediate 2 of the disk with the adhesive, removing the part corresponding to disk chambers 20, 21 with the laser cutting, and forming the fluid hole closing membrane 30 on the fluid hole region 10 by welding the upper portion substrate 1 and intermediate 2 of the disk 200 using this.

According to another embodiment of the present invention, the thin film closing membrane 30 in the upper portion substrate 1 of the disk 200 using the upper portion adhesive layer 1b which firstly adheres the membrane layer 1c the lower part adhesive layer 1d in which the part which firstly comes under disk chambers 20, 21 for the thin film closing membrane 30 formation is removed to the upper side of the intermediate 2 of the disk after doing the adhesion to the upper part thereafter corresponding to disk chambers 20, 21 and the fluid hole closing membrane 30 shape removed with the laser cutting. A fluid hole closing membrane 30 is formed on the first fluid hole 10 region by welding the first intermediate substrate 1 and intermediate substrate 2.

According to another embodiment of the present invention, patterning of adhesive layers 1b, 1d is caused by laser cutting or press cutting the chamber 20, 21 and fluid hole closing membrane 30.

According to embodiments of the present invention, FIGS. 1e through 1g, as a black membrane, display fluid hole opening/closing thin film valve 100 using black thermoplastic resin 40.

The thin film valve 100 includes an upper substrate 1, an intermediate substrate 2, and a lower substrate 3, and during the injection molding process, each substrate forms the first fluid hole 10 connecting the flow paths 22a 22c.

The substrates 1, 2, 3 are attached to each other in a close contact by the thin film adhesive tape layers 1a, 2a and form a thin film valve 100.

FIG. 1E_A to FIG. 1F_C shows a black hot melt adhesive is preferred as black thermoplastic resin 40 according to embodiments of the present invention Referring to FIG. 1E_A, and FIG. 1E_B, according to embodiment of the present invention, a thin film valve includes a second fluid hole 11 on the black thermoplastic resin 40 hole 11 and the first fluid hole 10 are connected each other and form a fluid hole.

According to an embodiment of the present invention, the first fluid hole 10 is closed or blocked by melting and removing the second fluid hole 11 formed on a black thermoplastic resin 40 by activating a laser beam generating system 107 or a laser module 103.

FIG. 1E_C shows open first fluid hole 10 and FIG. 1E_B shows closed first fluid hole 10 by removing the second fluid hole 11.

In preferred embodiment, the apparatus includes, melting the black thermoplastic resin 40 of the second fluid hole 11 into a gel state by activating the laser beam generator 107 or the laser module 103 and moving the black thermoplastic resin 40 toward the second fluid hold 11 using centrifugal force by rotating the disk to close the first fluid hole 10. Thereby, at the same time, the second fluid hole 11 is removed and the first fluid hole 10 is closed.

Referring to FIG. 1E_C, thin film 100 includes a membrane chamber 14, which stores a black thermoplastic resin 40, a first hole 10 which connects with the membrane chamber 14, where the membrane chamber has a space 13 where a room for the black thermoplastic resin to move in.

The laser beam generating unit 107 or the laser module 103 melts the black thermoplastic resin 40 to be a gel state.

By moving melted black thermoplastic resin 40 toward the first fluid hole, the first fluid hole is closed.

FIG. 1E_C shows a state where the first fluid hole 10 is open, FIG. 1E_B shows a state where the first hole 10 is closed.

Referring to FIG. 1F_A, FIG. 1F_B, and FIG. 1F_C, by operation of the laser beam generating unit 107 or the laser module unit 103, closing a first fluid hole 10 and opening the third fluid hole 12 at the same time by melting and removing the black thermoplastic resin 40 by a heat an embodiment of the present invention.

FIG. 1F_A shows that the first fluid hole 10 is open and the third fluid hole 12 is closed.

FIG. 1F_B shows that both the first fluid hole 10 and third fluid hole 12 are closed.

It is preferred to close the first fluid hole 10 by operating the laser beam generator 107 or laser module 103 and heating the black thermoplastic resin 40 into a gel state and then moving the black thermoplastic resin 40, by centrifugal force by rotating the disk, toward the first fluid hole 10 and closing or blocking the second fluid hole 11 according to an embodiment.

FIG. 1F_C-FIG. 1F_B show that the laser beam generating system 107 or the laser module 103 is moved toward the third fluid hole 12 and operated to open the third fluid hole 12 by a heat according to an embodiment.

Referring to FIG. 1F_B it is preferred that operating the laser beam-generating apparatus 107 or the laser module unit 103, melting the black thermoplastic resin 40 to be in a gel state by a heat by a laser beam, and then rotating the disk to move the melted black thermoplastic resin 40 toward the first fluid hole 10 by the centrifugal force, and opening the third fluid hole 12.

FIG. 1F_B shows that a laser beam generator 107 or a laser module 103 may easily open the third hole 12 since large portion of black thermoplastic resin 40 have been moved to the first hole 10 region as shown in FIG. 1F_C. When the third hole 12 is open, it is possible to move the liquid from the flow path 22a to the chamber 31.

That is, as shown in FIG. 1F_A, the liquid inputted from the flow path 22a can be moved to the opposite flow path 22c, while, in FIG. 1F_C, a liquid from flow path 22a can be transferred to the chamber 31 through the third hole 12.

In FIG. 1E_C, after the laser beam generating apparatus 107 or the laser module unit 103 is operated to melt the black thermoplastic resin 40 into a gel state, the melted black thermoplastic resin 40 is moved to the first fluid hole 10 by centrifugal force and closing the first fluid hole 10 at the same time opening the third fluid hole 12.

A thin film valve 100 shown in FIG. 1E_C may include the membrane chamber 14 to store black thermoplastic resin 40 to close a third hole 12, a space chamber 13 which connects with the membrane chamber 14 and provides a room for the black thermoplastic resin moved in.

The laser beam-generating apparatus 107 or the laser module unit 103 is operates to melt the black thermoplastic resin 40 and turns the resin into a gel state, and then rotates the disk to move the melted black thermoplastic resin 40 toward the first hole 10 for closing the same and opening the third hole 12.

FIG. 1G_A shows that the first hole 10 is opened and the third hole 12 is closed.

FIG. 1G_B shows that a first hole 10 is closed and a third hole 12 is opened.

In FIG. 1G_B, even if small amount of black thermoplastic resin 40 are remaining, the third fluid hole 12 can be easily open by the laser beam generator 107 or a laser module 103 because large portion of the black thermoplastic resin 40 have moved to the third fluid hole 12 due to centrifugal force.

When the third hole 12 is open, the liquid from the flow path 22a can be moved to the chamber 31. In other words, while, in FIG. 1k, injected liquid is transported from flow path 22a through the first fluid hole 10 to the fluid path 22c. In FIG. 1l, injected liquid is transported from flow path 22a to chamber 31 through the third fluid hole 12.

Figure 2A:
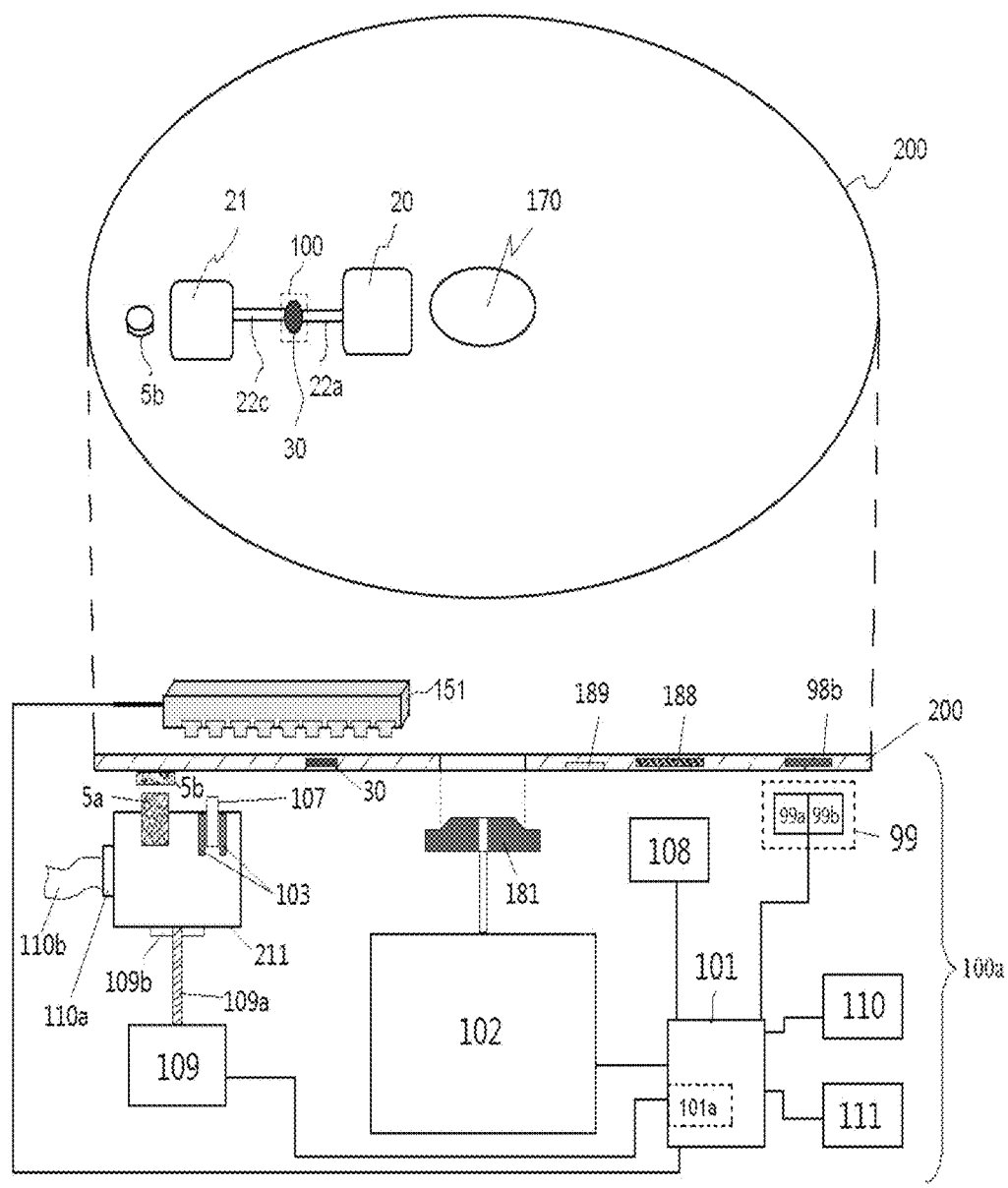
FIG. 2A and FIG. 2D show disk of thin film valve apparatus and controller of thin film valve apparatus according to an embodiment.

FIG. 2A shows a thin film valve apparatus includes a controller 100a and a disk 200 according to an embodiment.

FIG. 2A is an example applying the laser beam generator 107 as a heat source apparatus according to an embodiment.

Referring to FIG. 2A, specifically, an apparatus according to an embodiment of present application, may include chambers 20,21 to perform various chemical processes and store all kinds of the buffer solutions necessary for the analysis and fluid paths 22a, 22c to move a fluid and a buffer solution, a thin film valve 100 having a fluid hole closing membrane 30 to open and close a fluid path and a fluid hole, a motor 102 to control for rotating a disk 200, and a controller 100a to selectively open or close a plurality of valve by controlling a permanent magnet 5a and a laser beam controller 107.

Disc 200 is made up of upper substrate 1, intermediate substrate 2 and lower substrate 3 and surfaces of substrates 1,2,3 create plurality of fluid hole that connect flow path 22a 22c for fluid to flow, chamber 20,21 for storing buffer fluid and the fluid hole during injection molding process of substrates 1,2,3. The above substrates 1, 2, 3 are bonded to create the body of the disc 200.

A reference numeral 102 may be referred to a spindle motor or a stepper motor for rotating the disc 200. A reference numeral 201 is a slider 211 on which the movable permanent magnet 5a and a laser beam generator 107 mounted, wherein the slider 211 is controlled by a sliding motor 109 and worm gear connection parts 109a, 109b.

At the start and end of the biological or chemical process, for example, the preparation process, amplification process, mixing process, dilution process, labeling process, and the biological/chemistry reaction process or the cleaning process, independently on/off controller of a plurality of thin film valve can be achieved by melting the thin film membrane by operating the laser bream generator 107, after space addressing by a permanent magnet 5a installed on the slider 211.

According to another embodiment of the present invention, instead of laser beam generator 107 being mounted on the slider 211, a plurality of thin film valve corresponding one to one to a plurality of laser beam generators may be installed on the controller 100a.

At the start of end of biological or chemical process, independent on/off control of plurality of thin film valve can be achieved if the central controller 101 can independently control a plurality of laser beam generators installed on the controller 100a.

Moreover, the laser beam generator 107 may further include the focusing actuator 103 for varying a focal distance of the laser beam.

The central control apparatus 101 may further include the feedback controller 101a for measuring the intensity and amount of a laser beam passing through the thin film closing membrane 30 with the optical sensor and reflecting this to the focusing actuator 103.

According to an embodiment of the present invention, during closing/opening or thin film valve 100, the space addressing regarding the thin film valve 100 precedes radial direction and azimuthal direction space addressing of the disc 200.

The radial direction space addressing of the thin film valve 100 moves the slider 211 in reverse along the radial direction using the slider motor 109.

The slider 211 moves to the center of the disc 200 from the outside of the disc 200 or the direction of outside from the center of the disc 200 along the radial direction of the disc 200 by the slider motor 109.

A reference numeral 151 may be referred to a photo sensor array or a photo diode array for measuring the light quantity of the beam, generated by the laser beam generator 107, passing and coming out from the disk 200 or the thin film closing membrane 30.

According to an embodiment of the present invention, a linear image sensor, or a line image sensor, as an example, as the photo sensor array 151 senses the light quantity by unit of the pixel, is preferred. An embodiment of the present invention, a linear sensor array or a Contact Image Sensor CIS is preferred as the linear image sensor. However, it is not limited thereto.

The structure where the optical sensor the photo sensor array 151 lines up to the radial direction in a row is preferred. The photo sensor array may be installed face up with the laser beam generator 107 and disc is there between. The photo sensor array 151 measure the light quantity passes through the disc 200 or the thin film closing membrane 30 and comes out. The laser beam generator 107 is mounted on the slider 211 and it is transferable of the radial direction of the disc 200. Therefore it is necessary to have the photo sensor array 151 which lines up in the radial direction to measure the light quantity of the laser beam generator 107 in the position of the arbitrary radial direction.

An embodiment of the present invention, a space addressing of the azimuthal direction for the membrane valve 100 may be performed by radiating a continuous beam or a pulse beam outputted from the laser beam generator 107 on the disc 200 which is in a stationary state or a rotation operation state after the space addressing of the radial direction is completed.

In a state where the pulse beam or the continuous beam the radius direction space addressing described in the above is completed, it is preferred that whenever the thin film closing membrane 30 meets the laser beam if the laser beam generator 107 is continuously operated while rotating the disc 200, and then heats are accumulated by the beams and a fluid hole is opened.

According to an embodiment of the present invention, a method of opening a thin film valve using a continuous beam includes, in a state the radius direction space addressing as described above is completed, operating the laser beam generator 107 continuously while rotating the disc 200 at the same time rotating the stepping motor 102 slowly, the intensity of the light from the photo sensor array 151 becomes suddenly stronger, the search of the membrane valve 100 is achieved in the relevant position, The stepping motor 102 continually heats the thin film closing membrane 30 the rotation in the stop state and the perforation is opened.

In this case, it is preferred that it is covered with the CD label using the external side of the upper portion substrate 1 among substrates 1,2,3 except for the thin film closing membrane 30 or the lower part substrate 3 is the coating sheet or the light protection is coated.

Area except for the thin film closing membrane 30, the laser beam is blocked by the CD label or the light barrier coating. Thus, the photodiode array 151 can receive a strong light in a position of a perforation closing membrane 30. Compared to the other area of the disc 200, there is no adhesive layer at the thin film closing membrane 30 area. Thus, transmittance of light rate of the thin film closing membrane 30 is different from other area. Therefore, while the rotation of the disc 200, the intensity of a received light from the photo sensor array 151 suddenly can change in the thin film closing membrane 30 position and it can be used for searching a direction angle position of the thin film closing membrane 30.

Moreover, since the intensity of the received light from the photo sensor array 151 suddenly increases in a case the fluid hole is opened, the central control equipment 101 recognizes opening and closing of the fluid hole. If the intensity of light does not increase to enough extent even after enough heating it determines that there is an error and continues to the rotation of the disc 200 and the azimuth search toward the position of the membrane valve 100.

Another embodiment of the present invention, instead of the photo sensor array 151, an optical sensor arranged a reflection mode structure and the laser beam generator 107 may be mounted on the slider 211.

Another embodiment of the present invention, to make widening the opening area of perforation closing membrane 30 of the membrane valve 100, after the space addressing is completed and focusing the laser beam generator 107 by controlling the vertical direction with focusing actuator 103, opening the thin film closing membrane 30 by moving the laser beam generator 107 to right and left horizontal direction of the slider 211 number of millimeter or rotating disc 200 a little bit with the motor 102. In the direction angle position of the corresponding membrane valve 100 calculated based on the standard trigger signal in which the pulse beam is obtained with the azimuth detector 99, it periodically makes the operation on done the laser beam generator 107 is formed. The reference trigger signal refers as an azimuth reference.

An embodiment of the present invention, preferably, the azimuth detector 99 is a photo coupler. According to an embodiment of the present invention, it is preferred that the azimuth detector 99 is a reflection or translucent type.

An embodiment of the present invention, opening and closing method of the plurality of membrane valves 100, on the disc 200 with the laser beam generator 107 and permanent magnet 5a mounted on the slider 211, may be performed by the space addressing of the radial direction and space addressing of the azimuthal direction, respectively.

According to an embodiment of present invention, a plurality of membrane valves 100 and corresponding the photo diodes and laser beam generation systems of the plurality of membrane valves are accommodated in the control unit 100a, thereby opening and shutting of each of the plurality of the membrane valve may be controlled by the control unit.

According to an embodiment of present invention, a flexible cable 101b supplies the control signals for controlling the focusing actuator 103 and laser beam generator 107 on the slider 211, is connected to the central control equipment 101 through a harness 110a, harness and a feedback controller 101a supplies control signal for controlling a focusing actuator 103. Instead, a wafer can be used as the harness 110a. A turn table 181 may load the disc 200 through the central opening 170 by way of a front or a top loading.

A memory-embedded wireless radio frequency IC 188 may include the protocol, an analysis algorithm, a standard control value for the read, and location information about the assay site, the bioinformatics information, and the related information, self-diagnosis for the disc 200. Moreover, the identification ID of the disc 200 and individual encryption information can be stored on the memory-embedded wireless radio frequency IC 188 for not the disc used by an unauthorized person. The smart IC card form is preferred for the wireless radio frequency IC 188.

The information of the wireless radio frequency IC 188 is provided to the central controller 101 through a wireless transmission and may be used for the individual password. A radio wave generating unit 110 supplies power source to the wireless radio frequency IC 188.

An embodiment of the present invention, enough amount of the electricity is produced and supplied the power source to the wireless radio frequency IC 188 the electric wave by the reacts the induction coil installed in the wireless radio frequency IC 188 according to the Fleming's rule.

An embodiment of the present invention, the lighting device 108 may further included for supplying the light energy to the solar cell 189 on the disc 200. Preferably, the lighting device 108 is a high intensity LED module of multiple high intensity LEDs or a lamp.

Preferably, according to an embodiment of the present invention, through the wireless radio frequency IC 188, the specific identification of the disc 200 wirelessly is transmitted to central controller 101 at a loading point of time of the disc 200. The central controller 101 recognizes that the disc loaded in the control unit 100a of the thin film valve apparatus is an authenticated disk.

Preferably, according to an embodiment of the present invention, the controller 100a may further include the I/O unit 111. The I/O unit 111 may have one of the standards for telecommunications among group including USB Universal Serial Bus, the IEEE1394, ATAPI, the SCS I, IDE and wire and wireless internet communication network.

Figure 2B:
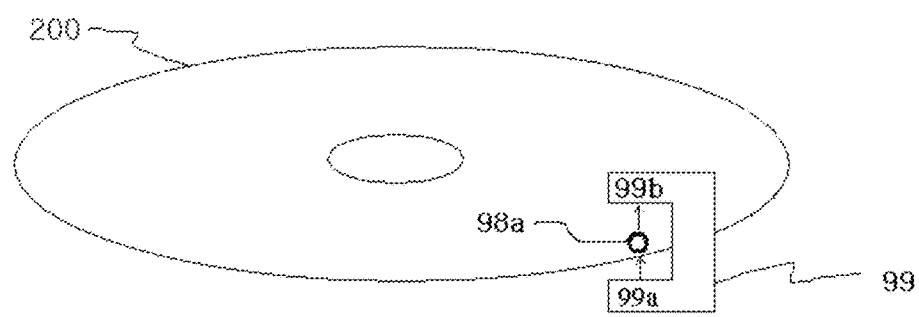
FIG. 2B shows azimuth detector according to an embodiment.
Figure 2B:
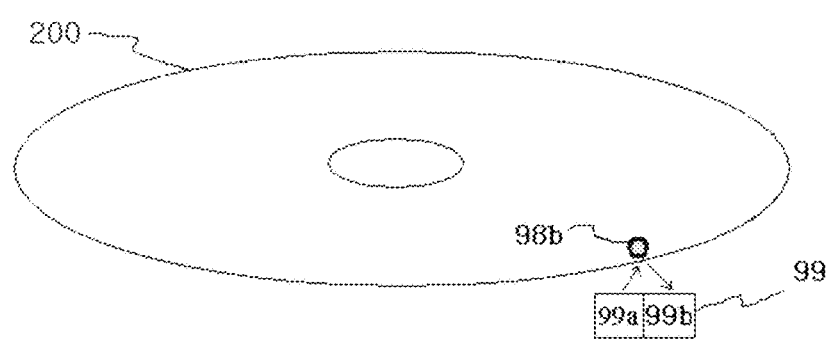

FIG. 2B shows an azimuth detector 99 according to an embodiment of the present invention. A pulse beam may be generated by periodically operating the laser beam generator 107 at the direction angle position of the corresponding membrane valve calculated based on a reference trigger signal from the azimuth detector 99. The reference trigger signal represents an azimuth reference of the disc 200.

A rotation angle position signal or a reference trigger signal may be obtained by the azimuth detector photo coupler 99 which includes the light generator 99a and an optical detector 99b.

Preferably, according to an embodiment of the present invention, the azimuth detector 99 may be a mirror projection or a translucent method. In case of the translucent, if only, the photo coupler 99 meets with the reference hole 98a on the disc 200 while rotating the disc 200, the reference trigger signal is generated and then provided to the central control equipment 101.

In case of the mirror projection, whenever the photo coupler 99 meets the reference reflector 98b for the rotation of the disc 200, the standard trigger signal is generated with the reference reflector 98b and photo coupler 99 and is provided to the central control equipment 101. Synchronized with the reference trigger signal, the central control equipment 101 operates the laser beam generator only at the position of the corresponding membrane valve and the corresponding membrane valve is selectively heated while rotating the disc 200.

Figure 2C:
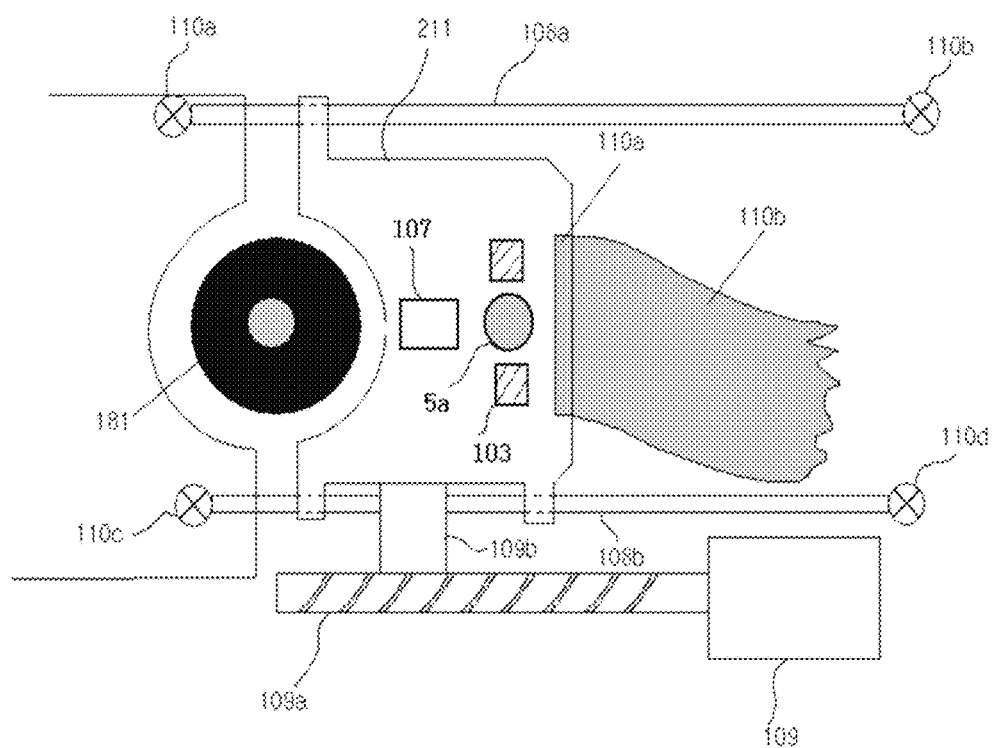
FIG. 2C shows laser beam generation system, permanent magnet and focusing actuator installed on the slider according to an embodiment.

FIG. 2C is an upper view of the slider 211 according to an embodiment.

According to an embodiment of the present invention, the laser beam generator 107, the permanent magnet 5a and focusing actuator 103 are installed arrange as shown. The slider 211 is transferred and controlled with worm gear connection parts 109a, 109b connected to the slide motor 109 shaft. The slider 211 slides down by using slide arms 108a, 108b as a guide.

The slide arms 108a, 108b are connected to the body of the control unit 100a through screws 110a, 110b, 110c, and 110d. The flexible cable 110b is connected to the central control equipment 101 with the wafer or the harness 110a. The turn-table 181 rotates with the motor 102.

Figure 2D:
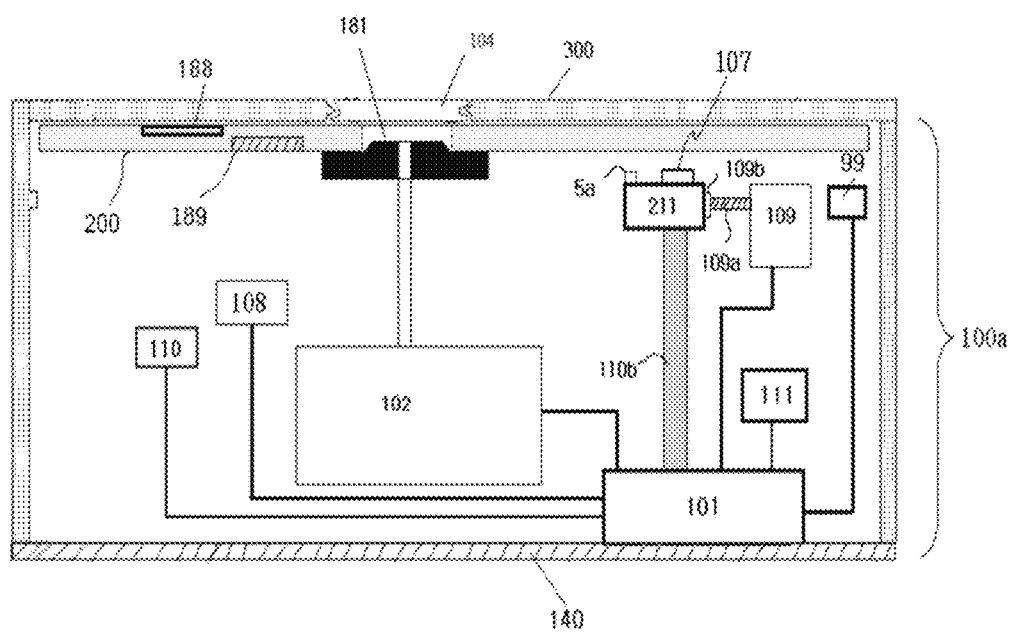

FIG. 2D shows a thin film valve apparatus includes a control unit 100a and the disc 200, according to an embodiment of present invention.

A body 300 supports control unit 100a. The circuit board 140 under the control unit 100a is connected to the control unit 100a. the central controller 101, which is an element of the a part of controller 100a, a radio wave generating unit 110, and the lighting device 108 and I/O unit 111 are installed on the circuit board 140.

The central controller 101 controls the motor 102 for the rotation or the pause of the disc 200, controls the laser beam generator 107 and movement of a permanent magnet 5a on the slider 211 by controlling the slide motor 109 and controls the laser beam generator 107 by periodically outputting a pulse beam at the direction angle position of the corresponding membrane valve calculated based on the standard trigger signal controlling the space transition of the and is obtained with the azimuth detector 99.

Preferably, according to an embodiment of the present invention, the central controller 101 may provide users' guide, according to the kind of the disc 200 loaded in the turn-table 181 of the control unit 100a and provide the user the audio synthesis for additional explanation to the user. Preferably, according to an embodiment of the present invention, the idle table 104 can compress on the disc 200 settled by in the turn-table 181 through the disc air gap with the magnetic force attractive force between the idle table and the turn-table 181, and move vertically and rotate idly.

Figure 2E:
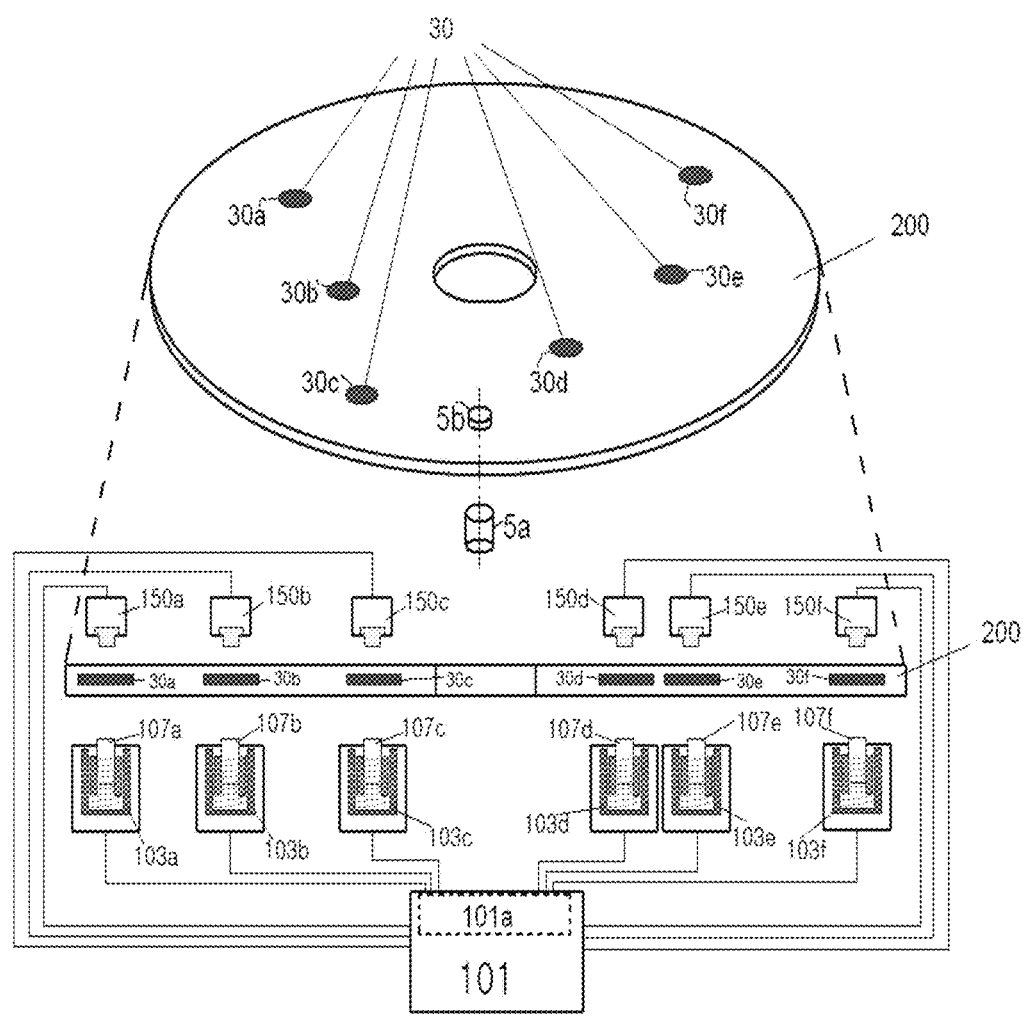
FIG. 2E shows independently controlling opening/closing of a plurality of fluid hole closing membranes on the disk according to an embodiment.

FIG. 2E is an apparatus for individually controlling opening and closing plurality of perforation closing membranes 30a, 30b, 30c, 30d, 30e, 30f arranged on the disc 200 an embodiment of the present invention.

Specifically, after addressing the space corresponding to the reference point of the disc based on thin film cylinder magnet 5a and permanent magnet 5b, utilizing each laser beam generators 107a, 107b, 107c, 107d, 107e, 107f corresponding to perforation closing membrane 30a, 30b, 30c, 30d, 30e, 30f of the thin film valve, the central controller 101 independently controls the on/off of each thin film valve.

According to an embodiment of the present invention, a laser beam to be focused on the surface of the thin film closing membrane 30 to concentrate a thermal energy.

Therefore, the thin film valve apparatus of the present invention includes laser beam generators 107a, 107b, 107c, 107d, 107e, 107f and focusing actuators 103a, 103b, 103c, 103d, 103e, 103f, for focusing laser beam corresponding to each thin film valve 100 on one side of the disc 200 and photo diodes to optical sensors on the other side of the disc to measure the quantity of the laser beams that came through the thin film closing membrane 30.

FIG. 2D is an embodiment of the present invention a laser beam generator and optical sensor which is arranged as the transmission mode structure to measure intensity of the light passing through the thin film closing membrane 30. According to an embodiment of the present invention, the focal distance of the laser beam of the focusing actuator 103 is controlled by an electromagnet coil and a permanent magnet.

According to an embodiment of the present invention, the focal distance of the laser beam the focusing actuator 103 is controlled by a piezo device. The scan focus mode which scans while the feedback controller 101a controls the focusing actuator 103 and varies the focal distance of the laser beam generator 107 with the maximum value in the minimum value and calculates the focal distance is preferred. In this case, the intensity of the laser light, which penetrates the thin film closing membrane 103 if the focus is correct among the scan process, is getting stronger. The feedback controller 101a receiving the change of this light through the optical sensor 150 with the feedback controls and focuses the focusing actuator 103.

Figure 2F:
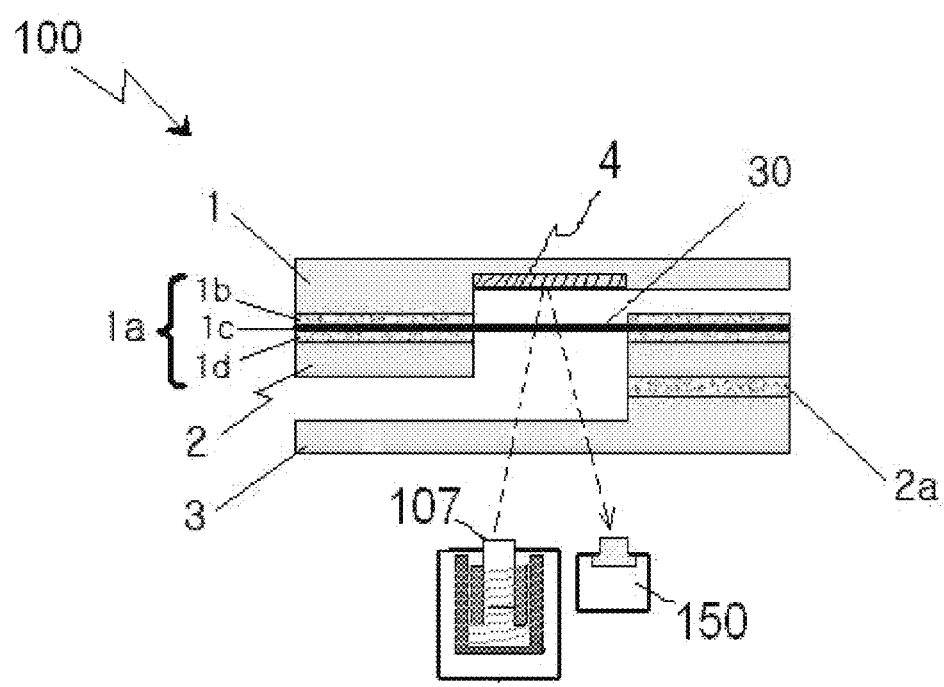
FIG. 2F shows the embodiment arranged as the reflection mode structure so that the laser beam generator and optical sensor measure the intensity of the light passing through the thin film closing membrane of the membrane valve using the thin film adhesive tape according to an embodiment.

Moreover, it is seen that after it focuses the thin film closing membrane is opened if the intensity of the light sensed with the optical sensor 150 becomes suddenly stronger. Referring to FIG. 2F_A to 2F_C, a reflective film 4 is further accommodated on the upper portion substrate 1 and both the laser beam generator 107 and optical sensor 150 are arranged in the reflection mode structure to measure the intensity of the light passing through the thin film closing membrane 30 of the perforation 10 site.

It is preferred to operate the laser beam generator 107 after the radial search and azimuthal direction search about the membrane valve 100 which the reflection mode structure opens and open the thin film closing membrane 30. In this case, the optical sensor 150 is accommodated under the disc 200 like as the laser beam generator 107 does. The intensity of the light in which reflected the optical sensor 150 has been turning the reflective film 4 back around is observed with the scan focus mode for the scan and the moment when the intensity of light becomes stronger unlike can know that it is easy to the focusing of the laser beam at the thin film closing membrane 30.

While scanning using the scan focus method, the optical sensor 150 determines the increase of the focus of the returned laser beam on the thin film closing membrane 30, by checking observing the intensity of beam reflected by the reflective film.

Moreover, whether or not the thin film closing membrane 30 is opened can be determined if the intensity of the light sensed with the optical sensor 150 becomes suddenly stronger after focusing.

Preferably, the reflective film are an aluminum, a gold, and a silver coating according to an embodiment of the present invention.

In the above, it described the embodiment doing with desirable of the present invention. But the invention is not restricted in the specific embodiment. That is, the multiple changes and correction about the invention if it grows up to go to the normal knowledge from the technical field in which the invention belongs thought and category of the attached patent claim are deviated from are made possible. And it should be considered that the equivalent of the correction and such all proper change s belong to the scope of the present invention.

An embodiment of the present invention, the lighting device 108 may further included for supplying the light energy to the solar cell 189 on the disk 200.

Preferably, the lighting device 108 is a high intensity LED module of multiple high intensity LEDs or a lamp.

Preferably, according to an embodiment of the present invention, through the wireless radio frequency IC 188, the specific identification of the disk 200 wirelessly is transmitted to central controller 101 at a loading point of time of the disk 200. The central controller 101 recognizes that the disk loaded in the control unit 100a of the thin film valve apparatus is an authenticated disk.

Preferably, according to an embodiment of the present invention, the controller 100a may further include the I/O unit 111.

The I/O unit 111 may have one of the standards for telecommunications among group including USB Universal Serial Bus, the IEEE1394, ATAPI, the SCS I, IDE and wire and wireless internet communication network.

FIG. 2B shows an azimuth detector 99 according to an embodiment of the present invention. A pulse beam may be generated by periodically operating the laser beam generator 107 at the direction angle position of the corresponding membrane valve calculated based on a reference trigger signal from the azimuth detector 99. The reference trigger signal represents an azimuth reference of the disk 200.

A rotation angle position signal or a reference trigger signal may be obtained by the azimuth detector photo coupler 99 which includes the light generator 99a and an optical detector 99b.

Preferably, according to an embodiment of the present invention, the azimuth detector 99 may be a mirror projection or a translucent method. In case of the translucent, if only, the photo coupler 99 meets with the reference hole 98a on the disk 200 while rotating the disk 200, the reference trigger signal is generated and then provided to the central control equipment 101.

In case of the mirror projection, whenever the photo coupler 99 meets the reference reflector 98b for the rotation of the disk 200, the standard trigger signal is generated with the reference reflector 98b and photo coupler 99 and is provided to the central control equipment 101.

Synchronized with the reference trigger signal, the central control equipment 101 operates the laser beam generator only at the position of the corresponding membrane valve and the corresponding membrane valve is selectively heated while rotating the disk 200.

FIG. 2C is an upper view of the slider 211.

According to an embodiment of the present invention, the laser beam generator 107, the permanent magnet 5a and focusing actuator 103 are installed as shown. The slider 211 is transferred and controlled with worm gear connection parts 109a, 109b connected to the slide motor 109 shaft. The slider 211 slides down by using slide arms 108a, 108b as a guide.

The slide arms 108a, 108b are connected to the body of the control unit 100a through screws 110a, 110b, 110c, and 110d. The flexible cable 110b is connected to the central control equipment 101 with the wafer or the harness 110a. The turn-table 181 rotates with the motor 102.

FIG. 2D shows a thin film valve apparatus includes a control unit 100a and the disk 200, according to an embodiment of present invention.

A body 300 supports control unit 100a. The circuit board 140 under the control unit 100a is connected to the control unit 100a. the central controller 101, which is an element of the a part of controller 100a, a radio wave generating unit 110, and the lighting device 108 and I/O unit 111 are installed on the circuit board 140. The central controller 101 controls the motor 102 for the rotation or the pause of the disk 200, controls the laser beam generator 107 and movement of a permanent magnet 5a on the slider 211 by controlling the slide motor 109 and controls the laser beam generator 107 by periodically outputting a pulse beam at the direction angle position of the corresponding membrane valve calculated based on the standard trigger signal controlling the space transition of the and is obtained with the azimuth detector 99.

Preferably, according to an embodiment of the present invention, the central controller 101 may provide users' guide, according to the kind of the disk 200 loaded in the turn-table 181 of the control unit 100a and provide the user the audio synthesis for additional explanation to the user. Preferably, according to an embodiment of the present invention, the idle table 104 can compress on the disk 200 settled by in the turn-table 181 through the disk air gap with the magnetic force attractive force between the idle table and the turn-table 181, and move vertically and rotate idly.

FIG. 2E is an apparatus for individually controlling opening and closing plurality of perforation closing membranes 30a, 30b, 30c, 30d, 30e, 30f arranged on the disk 200 an embodiment of the present invention.

Specifically, after addressing the space corresponding to the reference point of the disk based on thin film cylinder magnet 5a and permanent magnet 5b, utilizing each laser beam generators 107a, 107b, 107c, 107d, 107e, 107f corresponding to perforation closing membrane 30a, 30b, 30c, 30d, 30e, 30f of the thin film valve, the central controller 101 independently controls the on/off of each thin film valve.

According to an embodiment of the present invention, a laser beam to be focused on the surface of the thin film closing membrane 30 to concentrate a thermal energy.

Therefore, the thin film valve apparatus of the present invention includes laser beam generators 107a, 107b, 107c, 107d, 107e, 107f and focusing actuators 103a, 103b, 103c, 103d, 103e, 103f, for focusing laser beam corresponding to each thin film valve 100 on one side of the disk 200 and photo diodes to optical sensors on the other side of the disk to measure the quantity of the laser beams that came through the thin film closing membrane 30.

FIG. 2D is an embodiment of the present invention a laser beam generator and optical sensor which is arranged as the transmission mode structure to measure intensity of the light passing through the thin film closing membrane 30.

According to an embodiment of the present invention, the focal distance of the laser beam of the focusing actuator 103 is controlled by an electromagnet coil and a permanent magnet.

According to an embodiment of the present invention, the focal distance of the laser beam the focusing actuator 103 is controlled by a piezo device. The scan focus mode which scans while the feedback controller 101a controls the focusing actuator 103 and varies the focal distance of the laser beam generator 107 with the maximum value in the minimum value and calculates the focal distance is preferred. In this case, the intensity of the laser light, which penetrates the thin film closing membrane 30 if the focus is correct among the scan process, is getting stronger. The feedback controller 101a receiving the change of this light through the optical sensor 150 with the feedback controls and focuses the focusing actuator 103.

Moreover, it is seen that after it focuses the thin film closing membrane is opened if the intensity of the light sensed with the optical sensor 150 becomes suddenly stronger. Referring to FIG. 2f, a reflective film 4 is further accommodated on the upper portion substrate 1 and both the laser beam generator 107 and optical sensor 150 are arranged in the reflection mode structure to measure the intensity of the light passing through the thin film closing membrane 30 of the perforation 10 site. It is preferred to operate the laser beam generator 107 after the radial search and azimuthal direction search about the membrane valve 100 which the reflection mode structure opens and open the thin film closing membrane 30. In this case, the optical sensor 150 is accommodated under the disk 200 like as the laser beam generator 107 does.

While scanning using the scan focus method, the optical sensor 150 determines the increase of the focus of the returned laser beam on the thin film closing membrane 30, by observing the intensity of beam reflected by the reflective film 4.

Moreover, whether or not the thin film closing membrane 30 is opened can be determined if the intensity of the light sensed with the optical sensor 150 becomes suddenly stronger after focusing.

Preferably, the reflective film are an aluminum, a gold, and a silver coating according to an embodiment of the present invention.

In the above, it described the embodiment doing with desirable of the present invention. But the invention is not restricted in the specific embodiment. That is, the multiple changes and correction about the invention if it grows up to go to the normal knowledge from the technical field in which the invention belongs thought and category of the attached patent claim are deviated from are made possible. And it should be considered that the equivalent of the correction and such all proper change s belong to the scope of the present invention.

What is claimed:

1. A thin film valve apparatus, comprising:
   a plurality of chambers configured to store a fluid;
   a fluid path comprising a fluid hole, and connecting the plurality of chambers;
   a multilayered plurality of substrates forming the plurality of chambers, the fluid path, and the fluid hole;
   a black membrane configured to close the fluid hole;
   a laser beam generator disposed below a rotatable disk, and configured to output a laser beam to melt the black membrane to open the fluid hole;
   an optical sensor disposed proximate an upper or lower surface of the disk, and configured to measure an intensity of light passing through the fluid hole;
   an actuator configured to vary a focusing distance of the laser beam on the black membrane; and
   a feedback control device configured to turn off the laser beam generator, in response to the optical sensor measuring that the intensity of the light passing through the fluid hole exceeds a threshold,
   wherein the multilayered plurality of substrates, the flow path, the fluid hole, the plurality of chambers, and the black membrane are integrated into the disk.

2. The apparatus of claim 1, wherein a plurality of optical sensors is arranged in a line in a radial direction with respect to the disk, the laser beam generator is configured to slide in a radial direction with respect to the disk, the plurality of optical sensors is installed facing the laser beam generator so that the disk is disposed in between the plurality of optical sensors and the laser beam generator, and the plurality of optical sensor forms an array.

3. The apparatus of claim 1, wherein feedback control device is further configured to search for a location of the black membrane using azimuth search performed by rotating the disk, in response to the intensity of the light not exceeding the threshold after heating of the black membrane.

4. The thin valve apparatus of claim 1, further comprising a driving motor configured to rotate the disk, and a reflector or a film-shaped cylindrical magnet mounted on the disk and configured to provide a reference azimuth.

5. The thin film valve apparatus of claim 4, further comprising a slider configured to enable movement the laser beam generator and the optical sensor, a slide motor configured to control a movement of the slider in a radial direction with respect to the disk, and a central controller configured to control the laser beam generator, and the slide motor wherein the laser beam generator is further configured to selectively open and close the black membrane.

6. The apparatus of claim 4, wherein the feedback control device is further configured to selectively open the black membrane by turning on the laser beam generator based on the reference azimuth, which is determined by using the thin film cylinder magnet.

7. The apparatus of claim 1, wherein the disk is circular and further comprises a convex lens or a hemisphere lens, which is configured to focus the laser beam onto a position on the black membrane.

8. The apparatus of claim 1, wherein the fluid hole includes a reflector.

9. The apparatus of claim 1, wherein the disk comprises an RF IC configured to store any one of information from a protocol, an analysis algorithm, standard control values, location information for an analysis site, bioinformatics, personal encrypt information, and disk identification (ID).

10. The apparatus of claim 1, wherein the black membrane comprises one of black vinyl, black hot melt, black thermoplastic resin, black polyester film, black coated PVDF, black polyethylene film, Polypropylene, polyvinyl chloride, black PET polyethylene terephthalate, Poly-Ethylene-Terephthalate film, and other synthetic materials.

11. A method of controlling a valve, the method comprising:
    providing the thin film valve apparatus of claim 1;
    detecting a location of the black membrane on the disk;
    turning on the laser beam generator to output the laser beam at the detected location to melt the black membrane;
    measuring an intensity of the light passing through the fluid hole using the optical sensor to detect that the fluid hole is open;
    turning off the laser beam generator, by the feedback feedback control device, in response to the detecting that the fluid hole is open.

12. The thin film apparatus of claim 1, further comprising:
    a first adhesive layer comprising a first hole of the fluid hole; and
    a second adhesive layer comprising a second hole of the fluid hole that is aligned with the first hole,
    wherein the black membrane is disposed between the first adhesive layer and the second adhesive layer, is bonded to the first adhesive layer and the second adhesive layer, and blocks fluid communication between the first hole and the second hole.

* * * * *